(12) United States Patent
Lis et al.

(10) Patent No.: US 9,938,567 B2
(45) Date of Patent: Apr. 10, 2018

(54) HIGH-THROUGHPUT RNA INTERACTION ASSAY

(71) Applicants: John T. Lis, Ithaca, NY (US);
Abdullah Ozer, Vestal, NY (US);
Jacob M. Tome, Ithaca, NY (US)

(72) Inventors: John T. Lis, Ithaca, NY (US);
Abdullah Ozer, Vestal, NY (US);
Jacob M. Tome, Ithaca, NY (US)

(73) Assignee: Cornell University, Ithaca, NY (US)

(*) Notice: Subject to any disclaimer, the term of this patent is extended or adjusted under 35 U.S.C. 154(b) by 558 days.

(21) Appl. No.: 13/918,927

(22) Filed: Jun. 15, 2013

(65) Prior Publication Data
US 2014/0371080 A1 Dec. 18, 2014

(51) Int. Cl.
*G01N 33/543* (2006.01)
*C12Q 1/68* (2018.01)
*G01N 33/53* (2006.01)

(52) U.S. Cl.
CPC ....... *C12Q 1/6834* (2013.01); *G01N 33/5308* (2013.01)

(58) Field of Classification Search
None
See application file for complete search history.

(56) References Cited

U.S. PATENT DOCUMENTS 7,033,764 B2 * 4/2006 Korlach .............. C12Q 1/6869
435/183
2003/0176644 A1 * 9/2003 Byrd .................... C07K 14/245
530/350

OTHER PUBLICATIONS

Pavco et al (The Journal of Biological Chemistry, 1990. vol. 265, No. 17, pp. 9960-9969).*
Mahanty et al (The Journal of Biological Chemistry, 1998. vol. 273, No. 5, pp. 3051-3059).*
Illumina Sequencing Technology (Technology Spotlight: Illumina Sequencing Oct. 11, 2010).*
Guajardo & Sousa, "Characterization of the Effects of *Escherichia coli* Replication Terminator Protein (Tus) on Transcription Reveals Dynamic Nature of the Tus Block to Transcription Complex Progression," Nucleic Acids Res. 27(13):2814-2824 (1999).
Nutiu et al., "Direct Visualization of DNA Affinity Landscapes Using a High-Throughput Sequencing Instrument," Nat. Biotechnol. 29(7):659-664 (2011).
König et al., "Protein—RNA Interactions: New Genomic Technologies and Perspectives," Nature Reviews Genetics 13:77-83 (2012).
Nagarajan et al., "Sequencing and Genome Assembly Using Next-generation Technologies," Methods Mol Biol. 673:1-17 (2010).
Ansorge et al., "Next-generation DNA Sequencing Techniques," New Biotechnol. 25(4):195-203 (2009).
Niedringhaus et al., "Landscape of Next-generation Sequencing Technologies," Anal Chem. 83(12):4327-41 (2011).

* cited by examiner

*Primary Examiner* — Celine X Qian
(74) *Attorney, Agent, or Firm* — LeClairRyan, a Professional Corporation

(57) ABSTRACT

The present invention is directed to a method for detecting an interaction between a ribonucleic acid (RNA) molecule and a second molecule. This method involves providing a nucleic acid construct that contains a promoter sequence, a nucleotide sequence encoding the RNA molecule, and an RNA polymerase blocking site. The nucleotide sequence encoding the RNA molecule is transcribed in vitro to produce an RNA transcript corresponding to the RNA molecule. Transcription is halted by the RNA polymerase blocking site under conditions effective for the RNA transcript to remain tethered to the nucleic acid construct. The tethered RNA transcript is contacted with the second molecule and any interaction between the tethered RNA transcript and the second molecule is detecting and identified based on said contacting.

20 Claims, 11 Drawing Sheets

HIGH-THROUGHPUT RNA INTERACTION ASSAY

This invention was made with government support under grant numbers DA030329 and GM090320 awarded by the National Institutes of Health. The government has certain rights in this invention

FIELD OF THE INVENTION

The present invention relates to methods and kits suitable for identifying and characterizing interactions between a ribonucleic acid (RNA) molecule and a second molecule.

BACKGROUND OF THE INVENTION

Interactions between RNA and other factors are ubiquitous in biology (Castello et al., "Insights Into RNA Biology From an Atlas of Mammalian mRNA-Binding Proteins," *Cell* 149(6):1393-1406 (2012)). These interactions are postulated to play important roles in regulation of gene expression and in human disease (Lukong et al., "RNA-Binding Proteins in Human Genetic Disease," *Trends Genet.* 24(8): 416-425 (2008) and Estellar, M., "Non-Coding RNAs in Human Disease," *Nature Reviews Genetics* 12:861-874 (2011)). Several methods have been developed to probe the scope of and characterize these interactions (Martin et al., "Systematic Reconstruction of RNA Functional Motifs With High-Throughput Micro fluidics," *Nature Methods* 9:1192-1194 (2012) and Hafner et al., "Transcriptome-Wide Identification of RNA-Binding Protein and microRNA Target Sites by PAR-CLIP," *Cell* 141(1):129-141 (2010)), but a direct method for their high-throughput, quantitative characterization is lacking (König et al., "Protein-RNA Interactions: New Genomic Technologies and Perspectives," *Nature Review Genetics* 13:77-83 (2012)). The present invention is directed at overcoming this and other deficiencies in the art.

SUMMARY OF THE INVENTION

A first aspect of the present invention is directed to a method for detecting an interaction between a ribonucleic acid (RNA) molecule and a second molecule. This method involves providing a nucleic acid construct, the construct comprising a promoter sequence, a nucleotide sequence encoding the RNA molecule, and an RNA polymerase blocking site that is 3' to the nucleotide sequence encoding the RNA molecule. The method further involves transcribing the nucleotide sequence encoding the RNA molecule in vitro using an RNA polymerase to produce an RNA transcript corresponding to the RNA molecule, where the transcribing is halted at the RNA polymerase blocking site of the nucleic acid construct thereby tethering the RNA transcript to the nucleic acid construct. The tethered RNA transcript is contacted with the second molecule, and any interaction between the tethered RNA transcript and the second molecule is detected based on the contacting.

Another aspect of the present invention is directed to a kit for detecting an interaction between a ribonucleic acid (RNA) molecule and a second molecule. The kit contains one or more isolated nucleic acid constructs, each nucleic acid construct comprising a promoter sequence recognized by an RNA polymerase, a nucleotide sequence encoding an RNA molecule, and an RNA polymerase blocking site located 3' of the nucleotide sequence encoding the RNA molecule.

Another aspect of the present invention is directed to a method for screening a library of candidate compounds to identify a compound that binds to a target RNA molecule. This method involves providing a library of candidate compounds, and providing an isolated RNA transcript of the target RNA molecule tethered to a nucleic acid construct. The library of candidate compounds is contacted with the isolated RNA transcript tethered to the nucleic acid construct under conditions effective for one or more candidate compounds to bind to the RNA transcript. The method further involves detecting any binding interaction between one or more of the candidate compounds and the isolated RNA transcript tethered to the nucleic acid construct, and identifying the one or more candidate compounds that bind to the target RNA molecule based on the detection.

Identification of RNA molecules that bind to a target molecule of interest (i.e., proteins, peptides, small molecules) and the characterization of these interactions has been an important component of studying RNA function. Existing methods for studying RNA interactions include, electromobility shift assay (EMSA), fluorescence polarization, fluorescence correlation spectroscopy (FCS), and others. However, none of these assays are high-throughput or capable of processing multiple target molecules and millions of different RNAs at the same time. Described herein is a novel method of identifying and characterizing the affinity of interactions between RNA molecules and target molecules in a high-throughput manner. This method also provides kinetic information about these interactions (i.e., association and dissociation rate constants), and is fully adaptable to any of the high-throughput next-generation sequencing technologies. This compatibility not only allows one to obtain the sequence information of an RNA molecule before or after characterizing its interaction with another molecule, but also facilitates highly multiplexed detection of a plurality of RNA-target molecule interactions simultaneously.

BRIEF DESCRIPTION OF THE DRAWINGS

FIG. 1A is a schematic of the halting template. The 5' end has a promoter sequence (labeled 'Pro'), where the RNA polymerase initiates transcription. The sequence of this element depends on the polymerase being used. Downstream of this is the DNA template of the RNA to be halted. At the 3' end is the blocking site. This is the DNA sequence designed to cause a roadblock to transcription. It could be a binding site for a protein, a bulky group linked to a base of the DNA, or a crosslinking group. As shown in FIG. 1B, the first step in the halting process is functionalizing the blocking group. For example, in the case of a protein, this involves binding the protein to its DNA sequence element and in the case of crosslinking it involves inducing the crosslink. Transcription is then carried out as depicted in FIG. 1C. The RNA polymerase initiates transcription at the promoter sequence and the DNA template is transcribed up until the roadblock, where the polymerase is left stably halted with its bound RNA transcript. Finally, an RNA interacting factor (e.g., a protein, etc.) is bound to the halted, tethered RNA as shown in FIG. 1D.

FIG. 2A shows a map of the double stranded DNA template used for halting. The DNA template for the RNA to be halted (double line, labeled 'Target RNA Template') is flanked by a T7 promoter (labeled 'T7 Pro') and the Tus binding DNA sequence (labeled 'Ter'). As depicted in FIG. 2B, the first step in the process involves Tus binding to the Ter site. As shown in FIG. 2C, the T7 RNA polymerase is allowed to initiate transcription at the T7 promoter and transcribe through the target RNA template until it is stably halted at the Tus bound Ter site. Finally, as shown in FIG. 2D, a target RNA interacting factor (labeled as 'Target') is bound to the halted RNA. RNA interacting factors include proteins, peptides, lipids, nucleic acids, small molecules, or macromolecules.

FIG. 3A shows an example of anchoring the DNA template to a solid substrate at the end of the template distal to the RNA polymerase blocking site. Coupling can be either covalent or noncovalent (e.g., biotinylated DNA bound to avidin coated beads). FIG. 3B depicts an example of anchoring the DNA template to a solid substrate at the template end proximal to the RNA polymerase blocking site. As shown in FIG. 3C, the polymerase blocking group or protein can also be linked to the solid substrate. For example, a resin with affinity to a tag on a halting protein can immobilize the halting template via the blocking group. In another alternative, the halting template is immobilized via immobilization of the RNA polymerase as depicted in FIG. 3D. FIG. 3E shows the halted transcribed complex linked to a solid support via the transcribed RNA molecule, and FIG. 3F shows that the halted transcribed complex linked to a solid substrate through the second molecule or RNA interacting factor which is immobilized to a solid support.

FIG. 5A is a schematic illustration of a halted construct with a tethered RNA transcript of interest immobilized on the flow cell of the sequencer. During the sequencing process, clusters of DNA templates (i.e., roughly 2000 identical DNA sequences) are generated in an isothermal PCR reaction using oligonucleotide primers linked to the glass flowcell. The DNA templates of each cluster are made double stranded after sequencing and the RNA polymerase blocking site is functionalized by, for example, the binding of Tus to its Ter site present in every DNA template. T7 RNA polymerase initiates transcription at a T7 promoter site that is proximal to the covalent linkage of the DNA template to the glass flowcell, and transcribes the template encoding a GFP aptamer RNA or control RNA (SRB-2 aptamer) through the region of interest until it is halted by Tus. Labeled EGFP ("EGFP-mOrange") is added to the flowcell and allowed to interact with the halted RNAs. When the RNA transcribed is the GFP aptamer, EGFP binds to the RNA halted on the DNA as shown in FIG. 5A and the mOrange label of the EGFP-mOrange fusion protein is imaged using the TIRF optics of the sequencer. FIG. 5B shows an example where every DNA cluster sequenced has the GFP aptamer as the RNA transcribed. Clusters of halted transcript labeled with EGFP-mOrange show up as small spots in these images. Sequencing images (left panel of FIGS. 5B and 5C) were generated by imaging the fluorophores used during sequencing from one sequencing cycle, and thus show all clusters present in the region being imaged. The middle panel of FIG. 5B shows EGFP-mOrange imaging step after transcription and halting, and the right panel of FIG. 5B shows a merged image of the two steps. In cases where the RNA transcribed is the GFP aptamer, EGFP-mOrange localizes to almost every single cluster (FIG. 5B; center and right panels). FIG. 5C shows an example of RNA halting where the RNA transcribed does not have affinity to EGFP; this experiment is identical to that in depicted in FIG. 5B, except that the RNA transcribed is the SRB-2 aptamer. No localization of EGFP-mOrange fusion protein to clusters is observed, demonstrating the specificity of the RNA interaction in FIG. 5B.

$$\text{Intensity} = \text{Starting Intensity}\left(1 - \frac{\text{Cycle Number}}{\text{Characteristic Lifetime}}\right)$$

Figures 8A, 8B, 8C:
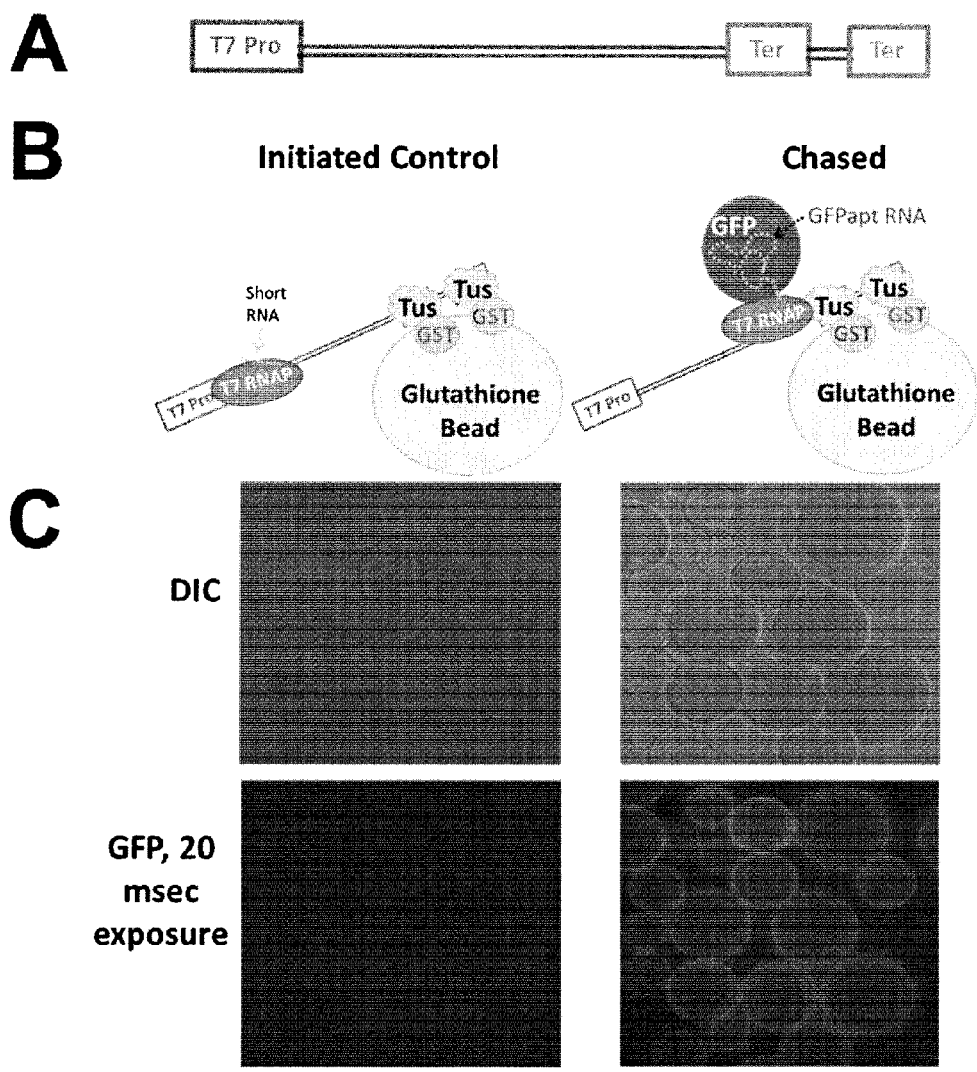

The characteristic lifetime of the halted complexes, or the time that it would take to decay to 1/e, or 36.8% of the initial RNAs thus corresponds to the negative inverse of the fitted slope. In this regime, halted complexes are decaying at a rate corresponding to a characteristic lifetime of 86 cycles. When the background fluorescence intensity of 98 is taken into account, this gives an actual characteristic lifetime of 20.4 imaging cycles, or 30.6 hours. Thus, 30.6 hours after transcription and washing, 36.7% of the initial halted RNA complexes would remain on the DNA template FIGS. 8A-8C demonstrate the functionality of halted RNAs. FIG. 8A is a schematic of the templates used for halting in this experiment. Templates contain a T7 promoter, the DNA template for the GFP aptamer, followed by two Ter binding sites. FIG. 8B is a schematic of the halted complexes. In both cases, single round transcription is carried out, that is there is a single T7 RNA polymerase and thus a single RNA transcript per DNA template. Transcription is initiated within a C-less cassette after the promoter; the first 11 nucleotides are all A, G, or T. Thus, in the absence of CTP, T7 polymerase initiates transcription, and transcribes 11 nucleotides before halting at the first C. In the chased sample, CTP was then added, allowing the polymerase to transcribe the rest of the template up to the Tus bound Ter site. In the initiated control, no CTP was added, giving just the 11 nucleotide RNA complexes. Both complexes are then bound to glutathione beads via the GST tag on Tus protein. Complexes were then incubated with EGFP. The initiated control does not display the full length GFP aptamer and thus unable to bind EGFP. The chased complexes do display the full length GFP aptamer and thus do bind EGFP. FIG. 8C are micrographs of glutathione beads bound to initiated and chased complexes. In the case of chased complexes but not the initiated complexes EGPF is bound to the surface of beads via the GST tag of Tus in the halted RNA complexes. This shows that halted complexes can be linked to solid substrate or purified by interactions with protein members of the complex.

Figures 9A, 9B:
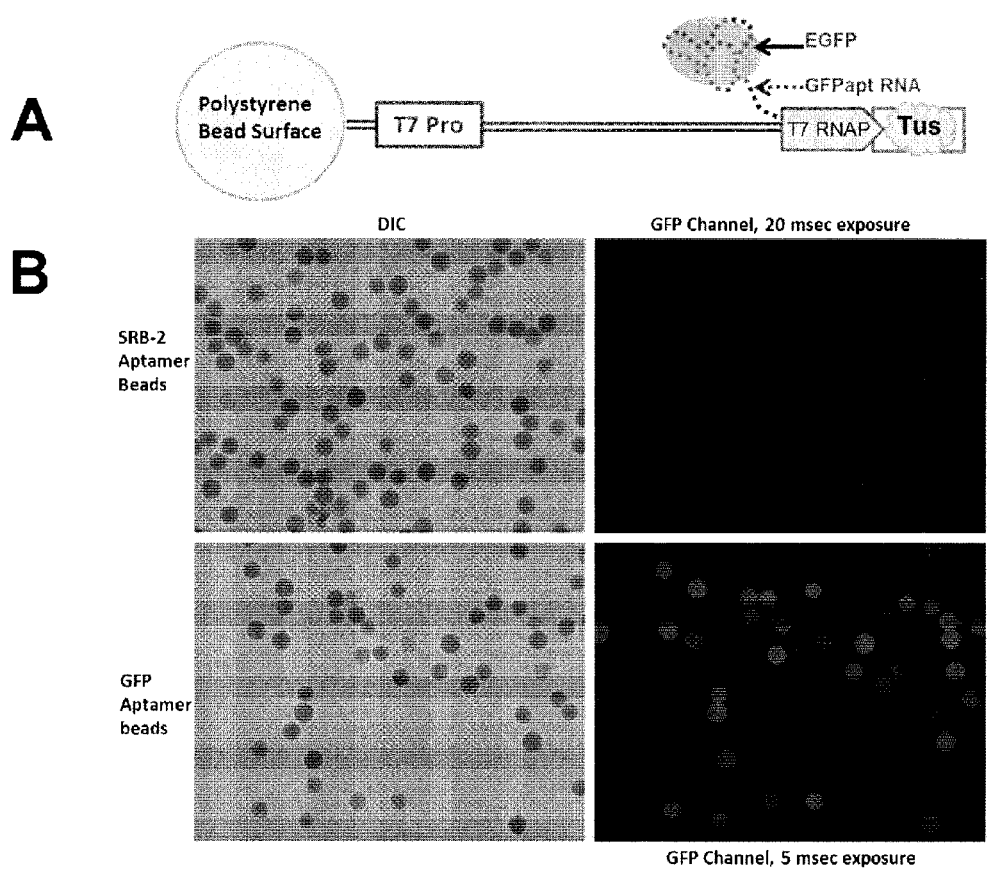

FIGS. 9A-9B show the functional halting of the GFP aptamer on polystyrene beads. FIG. 9A is a schematic of a halted complex immobilized on a polystyrene bead used in the 454 Life Sciences high-throughput sequencing technology. The DNA templates contain SRB or GFP aptamer flanked by a T7 promoter and Ter site. Following PCR, each bead is covered in thousands of identical DNAs. Transcription and halting was carried out, then followed by binding of EGFP. EGFP is able to bind the GFP aptamer coated beads via the halted GFP aptamer RNA, whereas SRB-2 aptamer RNA is unable to bind EGFP. FIG. 9B are fluorescence microscopy images confirming that EGFP binds GFP aptamer template beads via the halted RNA, while SRB-2 aptamer coated beads have no affinity for EGFP.

Figures 10A, 10B:
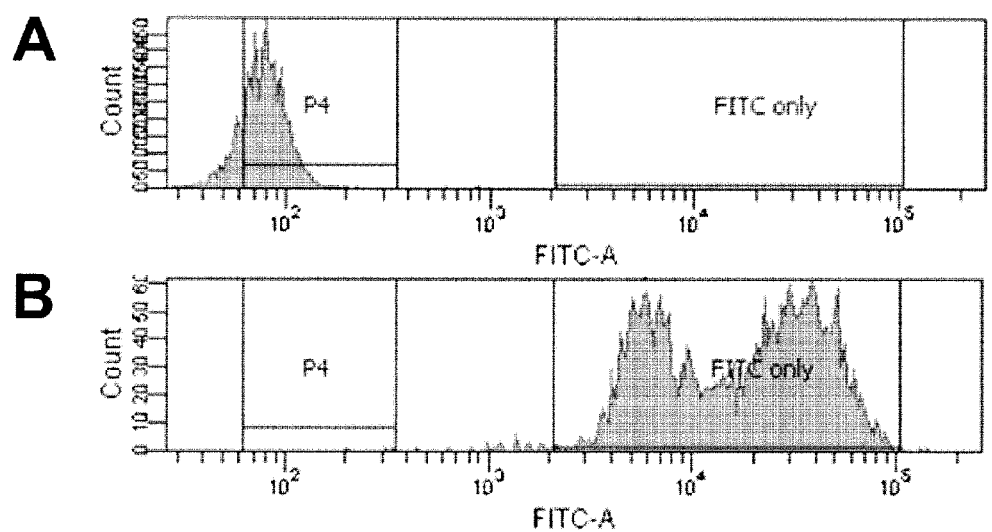
Figure 10C:
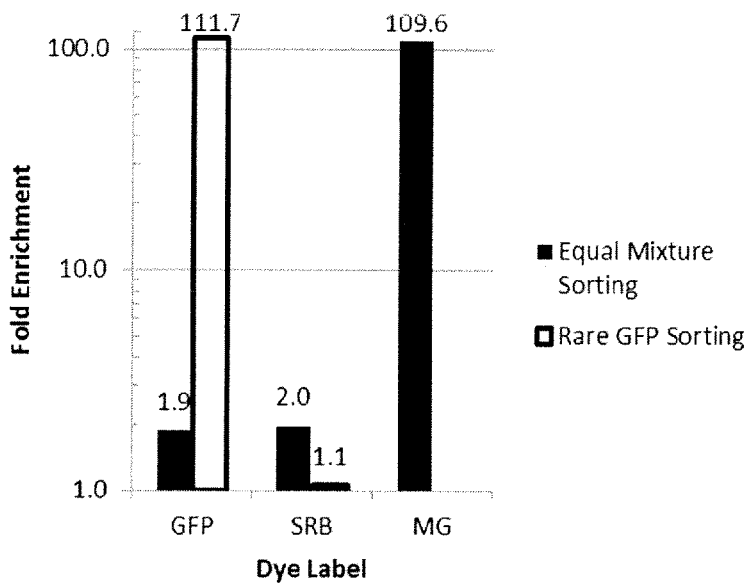
Figure 10D:
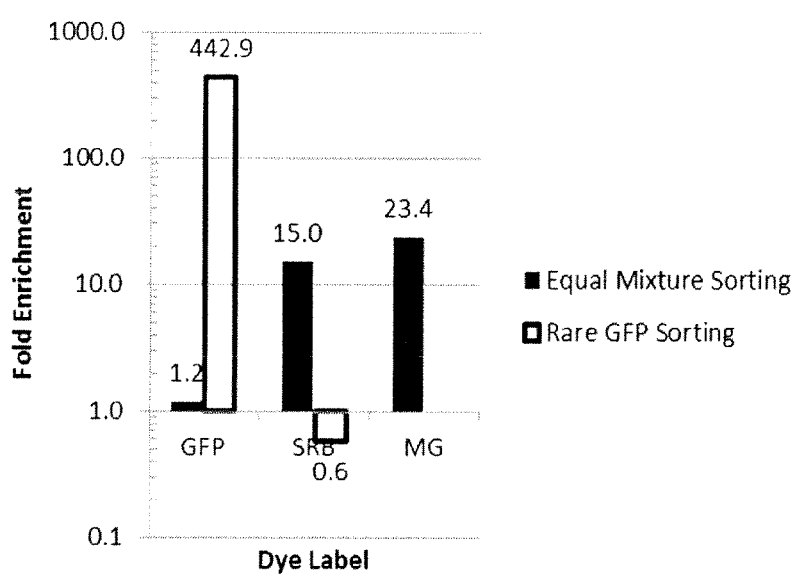

FIGS. 10A-10D show Fluorescence Activated Cell Sorting (FACS) of GFP aptamer beads. In FIG. 10A, the SRB-2 aptamer 454 Life Science beads shown in FIG. 9 were sorted by FACS. Flow cytometry traces of the FITC (GFP) channel show that SRB-2 aptamer beads have no appreciable binding to EGFP. FIG. 10B is flow cytometry trace of GFP aptamer template beads. All beads fluoresce with EGFP. Vertical lines labeled 'FITC only' show the cutoffs used for sorting GFP aptamer template beads. FIG. 10C is a graph showing qPCR-fold enrichment of GFP aptamer over background of 454 beads sorted by FACS. In equal mixture sorting, GFP aptamer beads labeled by transcription halting and binding of EGFP to the GFP aptamer were sorted from a 1:1:1:1 mixture of GFP aptamer beads labeled by EGFP:SRB-2 aptamer beads labeled by SRB dye:SRB-2 aptamer beads labeled by Malachite Green dye:random library beads. SRB-2 aptamer beads were labeled by nonspecific interaction of the dyes sulforhodamine and malachite green with the hydrophobic polystyrene beads. In rare GFP sorting, one drop of GFP aptamer beads (~20 µL) was added to 500 µL of a mixture of equal amounts of sulforhodamine B or malachite green labeled SRB-2 aptamer beads. qPCR for the GFP or SRB aptamer beads relative to nonspecific primer controls show that in the rare GFP aptamer bead case, sorting enriched for GFP aptamer beads 112 fold over the pre-sorted mixture. Enrichment in the case of equal beads was 1.9 fold. FACS sorting was also able to reliably separate the dye labeled SRB-2 aptamer beads. FIG. 10D is a graph showing qPCR fold enrichments of SRB aptamer over other non-specific template. In this case, fold enrichment over non-specific templates is shown. Thus, GFP aptamer beads fold enrichment is relative to SRB-2 beads, and vice versa. This metric shows 1.2 fold enrichment of GFP aptamer beads from an equal mixture and 443 fold enrichment of rare GFP aptamer beads.

DETAILED DESCRIPTION

A first aspect of the present invention is directed to a method for detecting an interaction between a ribonucleic acid (RNA) molecule and a second molecule. This method involves providing a nucleic acid construct, the construct comprising a promoter sequence, a nucleotide sequence encoding the RNA molecule, and an RNA polymerase blocking site that is 3' to the nucleotide sequence encoding the RNA molecule. The method further involves transcribing the nucleotide sequence encoding the RNA molecule in vitro using an RNA polymerase to produce an RNA transcript corresponding to the RNA molecule, where the transcribing is halted by the RNA polymerase blocking site of the nucleic acid construct thereby tethering the RNA transcript to the nucleic acid construct. The tethered RNA transcript is contacted with the second molecule, and an interaction between the tethered RNA transcript and the second molecule is detected based on the contacting.

Figures 1A, 1B, 1C, 1D:
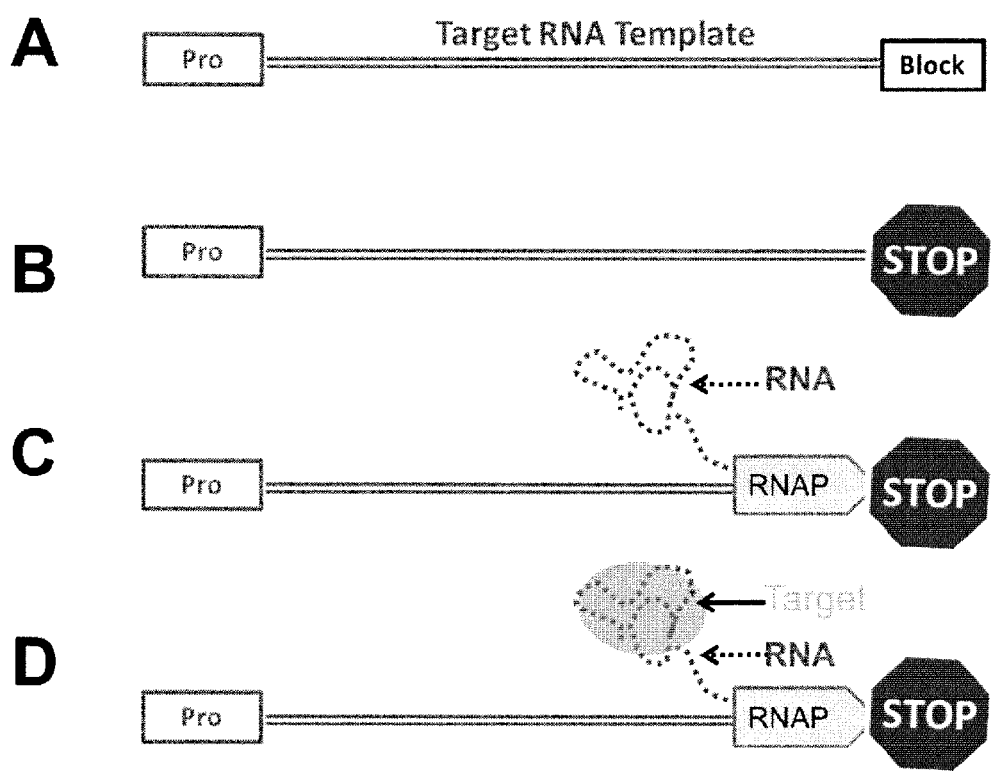
FIGS. 1A-1D depict the method of halting transcription in accordance with the present invention.

FIGS. 1A-1D schematically illustrate the method of the present invention. FIG. 1A shows the components of the nucleic acid construct, which is also referred to herein as the "halting template" or "DNA template". The nucleic acid construct is double-stranded (e.g., dsDNA), although a single-stranded template can also be employed as long as any elements that must be double-stranded (e.g., the promoter) are made so prior to initiating in vitro transcription. The nucleic acid construct typically comprises deoxyribonucleotides, however, modified deoxyribonucleotides or nucleotide analogues may also be incorporated. The 5' end of the construct contains a promoter sequence (labeled 'Pro'), where the RNA polymerase initiates transcription. The sequence of this promoter element depends on the polymerase being used. Typically the promoter sequence is between about 20 to about 200 nucleotides in length; however, shorter or longer promoter sequences are also envisioned. Numerous RNA polymerases and their corresponding promoter sequences are known in the art and suitable for use in this and all aspects of the present invention (see e.g., Jones et al., "Analysis of Clustered Point Mutations in the Human Ribosomal RNA Gene Promoter by Transient Expression In Vivo," *Proc Natl Acad Sci USA* 85(3): 669-673 (1988); Kerry et al., "Identification of Sequence Elements in the Human Cytomegalovirus DNA Polymerase Gene Promoter Required for Activation by Viral Gene Products," *J Virol.* 68(7): 4167-4176 (1994); Baer et al., "Structure and Transcription of a Human Gene for H1 RNA, the RNA Component of Human RNase P," *Nucleic Acids Res.* 18(1): 97-103 (1990); Auble et al., "Promoter Recognition by Escherichia coli RNA Polymerase. Effects of Substitutions in the Spacer DNA Separating the −10 and −35 Regions," *J Biol Chem.* 261(24):11202-6 (1986), which are hereby incorporated by reference in their entirety). Exemplary promoter sequences include, without limitation, the T7 promoter sequence, T3 promoter sequence, SP6 promoter sequence, RNA Pol I promoter sequence, RNA Pol II promoter sequence, RNA Pol III promoter sequence, and *E. coli* RNA polymerase promoter sequence. The minimum core nucleotide sequence for each of the aforementioned promoters is shown in Table 1 below. Variants of the minimum promoter sequences, i.e., promoter sequences containing nucleotide additions and/or substitution to modify promoter strength, are well known in the art and suitable for use in this and all aspects of the present invention. The promoter sequence can be added to the DNA template using anyone of a variety of enzymatic reactions known in the art, for example, polymerase chain reaction (PCR), blunt end ligation, restriction digestion and ligation, or recombination.

of the nucleotide sequence encoding the RNA molecule of interest (FIG. 1A; "Block"). This is a DNA sequence designed to cause a roadblock to transcription by halting the progression of an RNA polymerase. As described in more detail below, the roadblock may be one or more bulky groups linked to a base of the DNA, one or more crosslinking groups, or one or more binding sites for one or more proteins.

In one embodiment of the present invention, the roadblock is a covalently bound blocking group that is incorporated in the DNA template itself. Such a template would contain a large, bulky moiety covalently attached to a base of the template strand of dsDNA. The moiety can be added to the template by constructing the DNA template using PCR with one primer that had been synthesized with the blocking group added to one or more of its bases. Suitable blocking groups include, without limitation, metabolites of PAH benzo[c]phenanthrene (BPh) which form bulky DNA adducts at adenine bases (BPh-dA) and block RNA polymerase progression (Schinecker et al., "Human RNA Poly-

TABLE 1

Minimum Promoter Sequences of Exemplary RNA Polymerases

| Promoter Name | Promoter Sequence |
| --- | --- |
| T7 | TAATACGACTCACTATAG(+1)G (SEQ ID NO: 1) |
| T3 | AATTAACCCTCACTAAAG(+1)G (SEQ ID NO: 2) |
| SP6 | ATTTAGGTGACACTATAG(+1)A (SEQ ID NO: 3) |
| RNA Pol I | ACGGGCCGGCCCCTGCGTGTGGCCAGGGCGGCCGGGAGG GCTCCCCGGCCCGGCGCTGTCCCCGCGTGTGTCCTTGGGTT GACCAGAGGGCCCCGGGCGCTCCGTGTGTGGCTGCGATGG TGGCGTTTTTGGGGACAGGTGTCCGTGTCGCGCGTCGCCT GGGCCGGCGGCGTGGTCGGTGACGCGACCTCCCGGCCCCG GGGAGGTATATCTTTCGCTCCGAGTCGGCATTTTGGGCCG CCGGGTTATTG(+1)CTGACACGCTGTCCTCTGGCGACCTGT CGCTGGAGAGGTTGGGCCTCCG (SEQ ID NO: 4) |
| RNA Pol II | GCTGCAGAACCTCTTTCCCTATCTGGTGTCCGCCGACGGG ACCACCGTGACGTCGGGCAGCACCAAAGACACGTCGTTAC AGGCTCCGCCTTCCTACGAGGAAAGTGTTTATAATTCTGGT GGCAAAGGACCGGG(+1)ACCACCGTCGTCTGATGCAT (SEQ ID NO: 5) |
| RNA Pol III | ACAGGGGAGTGGCGCCCTGCAATATTTGCATGTCGCTATG TGTTCTGGGAAATCACCATAAACGTGAAATGTCTTTGGAT TTGGGAATCTTATAAGTTCTTATGAGACCACTCTTTCCCA (+1)TAGGGCGGAGGGAAGCTCA (SEQ ID NO: 6) |
| E. Coli RNA Pol | AATTCATAGTCAACACGCACGGTGTTAGACATTTATCCCTT GCGGCGATAGATTTAACGTA(+1)TGAGCACAAAAAAGAAA CCATTG (SEQ ID NO: 7) |

Downstream of the promoter sequence is a nucleotide sequence encoding the RNA molecule of interest (see FIG. 1A; "Target RNA Template"). The nucleotide sequence may encode any RNA molecule of interest including, without limitation, a message RNA (mRNA), pre-mRNA, a non-coding RNA (ncRNA), e.g., ribosomal RNA (rRNA), transfer RNA (tRNA), small nuclear RNA (snRNA), small nucleolar RNA (snoRNA), small interfering RNA (siRNA), piwi-interacting RNA (piRNA), microRNA (miRNA), antisense RNA (aRNA), CRISPR RNA (crRNA), long noncoding RNA (lncRNA), etc., an aptamer, an enhancer region, a random sequence, or a transcript of any genomic DNA fragment.

The nucleic acid construct utilized in the methods of the present invention further contains an RNA polymerase blocking site or "roadblock" that is located 3' or downstream merase II is Partially Blocked by DNA Adducts Derived from Tumorigenic Benzo[c]phenanthrene Diol Epoxides: Relating Biological Consequences to Conformational Preferences," *Nucl. Acids Res.* 31(20):6004-15 (2003), which is hereby incorporated by reference in its entirety), thymine glycol (Tornaletti et al., "Effect of Thymine Glycol on Transcription Elongation by T7 RNA Polymerase and Mammalian RNA polymerase II," *J Biol Chem.* 276(48):45367-71 (2001), which is hereby incorporated by reference in its entirety), N2-ethyl-2'-deoxyguanosine (N2-Et-dG) (Cheng et al., "Differential Blocking Effects of the Acetaldehyde-Derived DNA Lesion N2-ethyl-2'-deoxyguanosine on Transcription by Multisubunit and Single Subunit RNA Polymerases," *J Biol Chem.* 283(41):27820-8 (2008), which is hereby incorporated by reference in its entirety) and an abasic site (no nucleotide base) (Tornaletti et al., "Transcription Arrest at an Abasic Site in the Transcribed Strand of Template DNA," *Chem Res Toxicol.* 19(9):1215-20 (2006), which is hereby incorporated by reference in its entirety). When the RNA polymerase encounters the blocking moiety, further transcription of the downstream nucleotide sequence is halted. The blocking moiety preferably does not cause the release of the RNA polymerase or RNA transcript such that the RNA transcript remains tethered to the nucleic acid construct.

In another embodiment of the present invention, a cross-linking molecule is used to covalently link the two DNA strands thereby blocking the progression of an RNA polymerase. The cross-linking molecule can be incorporated during synthesis by an oligonucleotide primer used to construct the nucleic acid construct. Such a group can be induced to covalently link itself to the opposite strand of DNA. For example, 5-bromouridine can be introduced into the template and induced to crosslink to the other strand of template by exposure to UV light. Alternatively site-specific alkane-disulfide DNA interstrand crosslinks can be incorporated to link the two DNA strands (Santangelo et al., "Formation of Long DNA Templates Containing Site-Specific Alkane-Disulfide DNA Interstrand Cross-Links for use in Transcription Reactions," *Methods Enzymol.* 371:120-32 (2003), which is hereby incorporated by reference in its entirety). When the RNA polymerase encounters the cross-link, further transcription of the downstream nucleotide sequence is halted. The blocking crosslink preferably does not cause the release of the RNA polymerase or RNA transcript such that the RNA transcript remains tethered to the nucleic acid construct.

In yet another embodiment of the present invention, the RNA polymerase blocking group is a DNA binding protein sequence that specifically binds a DNA binding protein capable of blocking transcription by the RNA polymerase while not causing the release of the previously transcribe RNA molecule (i.e., the RNA transcript remains tethered to the halted RNA polymerase). One salient feature of these protein factors is an ability to bind their specific DNA sequence element with extremely high affinity specificity and stability. If the stability of this interaction is sufficiently high, the polymerase's helicase activity will not be sufficient to disrupt it, thus preventing the RNA polymerase from transcribing through the complex. Proteins capable of this activity when bound to their corresponding sequence element include but are not limited to lacI protein, a non-cleaving mutant of EcoRI endonuclease, e.g., Gln-111 mutant of EcoRI endonuclease (Pavco et al., "Characterization of Elongating T7 and SP6 RNA Polymerases and their Response to a Roadblock Generated by a Site-Specific DNA Binding Protein," *Nucleic Acids Res.* 19(17):4693-46 (1991), which is hereby incorporated by reference in its entirety), polyoma virus T antigen, CCAAT box protein, TTFI, mycophage L5 repressor, and bacterial replication terminator proteins (King et al., "Using a lac Repressor Roadblock to Analyze the *E. Coli* Transcription Elongation Complex," *Methods in Enzymology* 371:207-218 (2003), which is hereby incorporated by reference in its entirety).

Bacterial replication terminator proteins are DNA binding proteins responsible for polar termination of DNA replication forks at the replication termination site in bacterial genomes (Kamada et al., "Structure of a Replication-Terminator Protein Complexed with DNA," *Nature* 383(6601): 598-603 (1996), which is hereby incorporated by reference in its entirety). In this system, replication of a circular bacterial genome begins at a defined site and radiates outward bidirectionally. At the site of termination of replication (hereafter referred to as ter), the replication terminator protein binds its ter sequence element. It prevents replication through this site in one direction by interrupting the helicase activity of the replication fork in a polar manner. Forks replicating in the opposite direction, however, are able to proceed past the replication terminator protein/ter complex. Thus, it is referred to as a polar contrahelicase.

In addition to halting DNA replication, replication terminator proteins have also been shown to stop RNA polymerases from transcribing through ter sites (Mohanty et al., "The Relationship Between Sequence-Specific Termination of DNA Replication and Transcription," *EMBO J.* 15(10): 2530-2539 (1996), which is hereby incorporated by reference in its entirety). As demonstrated herein, RNA polymerase transcription in the nonpermissive direction through a Tus/Ter replication terminator protein complex is efficiently halted, and the polymerase remains upstream of the DNA/protein complex site with the RNA transcript still bound most likely in a backtracked elongation complex.

A number of replication terminator proteins and their corresponding binding-sites have been identified in a wide variety of Gram positive and Gram negative microorganisms (see U.S. Patent Application Publication No. 20030176644 to Byrd et al., Bussiere, et al., "Termination of DNA Replication of Bacterial and Plasmid Chromosomes," *Mol. Micro.* 31(6):1611-1618 (1999) and Griffiths, et al., "Replication Terminator Protein-Based Replication Fork-Arrest Systems in Various *Bacillus* Species," *J. Bacteriology* 180 (13):3360-3367 (1998), which are hereby incorporated by reference in their entirety). Exemplary replication terminator proteins suitable for use in the present invention include, without limitation the *Bacillus subtilis* replication terminator protein (RTP) and its IRI and IRII binding sequences (Lewis et al., "Identification of the Replication Terminator Protein Binding Sites in the Terminus Region of the *Bacillus subtilis* Chromosome and Stoichiometry of the Binding," *J. Mol. Biol.* 214(1):73-84 (1990), which is hereby incorporated by reference in its entirety), and *Escherichia coli* terminus utilization substance protein (Tus) and its Ter-binding sequence (Neylon et al., "Replication Termination in *Escherichia coli*: Structure and Antihelicase Activity of the Tus-Ter Complex," *Microbiol. Mol. Biol. Rev.* 69(3):501-526 (2005), which is hereby incorporated by reference). However, any other known replication terminator proteins and their corresponding DNA-binding sites are suitable for use in the methods and nucleic acid constructs of the present invention. The nucleotide and amino acid sequences of these replication terminator DNA binding sites and binding proteins are readily known and available in the art.

RNA polymerase blocking sites comprising DNA binding sequences can be added to the DNA halting template using anyone of a variety of enzymatic reactions known in the art, for example, PCR, blunt end ligation, restriction digestion and ligation, or recombination.

The nucleic acid construct utilized in the methods of the present invention may further contain a "spacer sequence". The spacer sequence is located between the nucleotide sequence encoding the RNA of interest and the RNA polymerase blocking site. The spacer sequence can be any random, short (~15-50 nucleotide base pairs) nucleotide sequence that functions as a landing pad for the RNA polymerase following transcription of the RNA molecule of interest. It serves to ensure the entire RNA molecule of interest is transcribed and out of the RNA polymerase prior to RNA polymerase halting.

FIGS. 1B-1D show the basic steps involved in carrying out the transcription halting process of the present invention.

These steps can be carried out sequentially or all at once in a single in vitro transcription halting reaction. As depicted in FIG. 1B, the first step involves functionalizing the blocking group, i.e., the functional RNA polymerase blocking moiety must be added or incorporated into the nucleic acid construct. In the case of bulky moieties which are covalently linked to DNA, the large groups are functional upon incorporation into the DNA. In the case of crosslinking molecules, the crosslink can be induced, by exposure to UV light, for example. Finally, in the case of roadblocking proteins, the protein is bound to the DNA template. In accordance with this embodiment, the binding protein is first expressed and purified by standard molecular biology techniques, then bound to the DNA template under conditions that are conducive to this binding event.

The second step of the process involves transcription of the nucleic acid construct as shown in FIG. 1C. This can be accomplished by combining the required components of an in vitro transcription reaction, i.e., RNA polymerase (e.g., T7 RNA polymerase, *E. coli* RNA polymerase, RNA Pol I, RNA Pol II, RNA Pol III, SP6, T3 RNA polymerase, or any other known RNA polymerase), ribonucleotide triphosphates (NTPs), and the appropriate buffer with the nucleic acid construct containing the promoter sequence, DNA template encoding the RNA of interest, and polymerase blocking site. The RNA polymerase binds to the promoter and initiates transcription. The polymerase transcribes through the template up to the roadblock where it becomes stably halted. Once transcription has taken place, halted RNA complexes can optionally be purified, i.e., removed from the transcription reaction components to enhance the stability of the halted complex. Purification can be achieved by any number of separation techniques such as size exclusion chromatography, gradient centrifugation, or coupling to a solid substrate followed by washing.

In one embodiment of the present invention, a single reaction mixture containing every component needed for transcription can be utilized. Under this paradigm, referred to as multiple round transcription, polymerases are capable of undergoing multiple cycles of initiation, elongation, and termination on each template. Alternatively, a single round transcription reaction strategy, which separates the step of initiation from elongation and termination can be utilized. Under this paradigm, each DNA template is subjected to the transcription cycle only once. This is most often accomplished by withholding one nucleotide from the transcription mix, with a template containing a short cassette lacking the withheld nucleotide downstream of the RNA polymerase promoter sequence. The RNA polymerase is able to initiate and transcribe through the cassette, but is halted in a backtracked state upon encountering the site of the base that is lacking in the reaction mix. After achieving this state, the transcription complexes are then subjected to conditions that allow for elongation through the rest of the template up to the site of the halting (i.e., RNA polymerase blocking site), but is not permissive to more initiation on the DNA templates. The ability to elongate is facilitated through addition of the withheld nucleotide.

Preventing multiple rounds of transcription or transcription reinitiation can also be achieved by either depleting additional polymerases from the reaction solution, or by adding a specific inhibitor of reinitiation. Depletion of RNA polymerase from a reaction mix can be achieved by exchanging the transcription reaction mixture following initiation with a reaction mixture lacking RNA polymerases, but containing the all four NTPs. This is readily carried out when one component of the transcription reaction is coupled to a solid support as shown in FIGS. 3A-3F. Bound RNA polymerases will then elongate through the template to the blocking site where they will become stably halted. Because very few polymerases will terminate, there will be very few free RNA polymerase molecules in solution, making reinitiation on any given halting template very unlikely.

Alternatively, reinitiation can be prevented by using a chemical inhibitor of RNA polymerase initiation such as heparin. In this case, there is no need to exchange the solution between the initiation and elongation steps of the transcription cycle. Rather, the inhibitor of initiation is added along with the fourth nucleotide, allowing elongation through the template to the roadblock. Further initiation on each DNA template is prevented by the inhibitor.

Single round transcription is useful for halting transcription, because it allows for at most one polymerase to be engaged on each DNA template. Under this paradigm, a larger fraction of the RNAs synthesized are stably halted on their respective DNA templates; however the total fraction of DNA templates with a halted transcript will be lower than under multiple round transcription. This low rate of termination is due to an inability of multiple polymerases to cooperatively induce termination on a single DNA (Epshtein et al., "Transcription Through the Roadblocks: The Role of RNA Polymerase Cooperation," *EMBO J.* 22:4719-4727 (2003), which is hereby incorporated by reference in its entirety). Thus, a single round transcription approach is most useful where one does not want to generate free transcripts present in the solution where they could compete with halted, immobilized RNAs for interaction with the target being assayed.

The final step of the method of the present invention involves contacting the halted complex comprising the tethered RNA transcript with the second molecule as shown in FIG. 1D. The second molecule is any factor that may potentially interact with the RNA transcript of interest. The second molecule can be any biological or nonbiological factor. For example, the second molecule may be a protein, polypeptide, or peptide, a lipid, a deoxyribonucleic acid (DNA) molecule, an RNA molecule, a small molecule, or a macromolecule.

In accordance with this aspect of the present invention, the second molecule contains a label to facilitate the detection of its interaction with the tethered RNA transcript. Suitable labels that can be coupled to or incorporated within the second molecule include, without limitation, a fluorescent label, a radiolabel, a chemiluminescent label, and a luminescent label. Suitable radiolabels include, without limitation, bismuth ($^{213}$Bi), carbon ($^{14}$C) chromium ($^{51}$Cr), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn). Methods of radiolabeling molecules, are well known in the art, see e.g., U.S. Pat. No. 5,830,431 to Srinivasan et al., which is hereby incorporated by reference in its entirety. Radioactivity is detected and quantified using a scintillation counter or autoradiography. Suitable fluorescent labels include, without limitation, umbelliferone, fluorescein and derivatives thereof, fluorescein isothiocyanate, rhodamine and derivatives thereof, dichlorotriazinylamine fluorescein, dansyl chloride or phycoerythrin. Examples of luminescent labels include, but are not limited to, luminol, luciferase, luciferin, and aequorin. Fluorescent and luminescent labels can be conjugated to second molecule of the present invention using techniques disclosed in CURRENT PROTOCOLS IN IMMUNOLOGY (Coligen et al. eds., 1991), which is hereby incorporated by reference in its entirety. Fluorescence and luminescence can be detected and quantified using a fluorometer or luminometer.

Other labels suitable for labeling and detecting the second molecule include, without limitation, enzymes (that need a reaction with a substrate to be detected), specific binding pair components (such as avidin, streptavidin, and/or biotin), biocytin, iminobiotin, colloidal dye substances, reducing substances (eosin, erythrosine, etc.), digoxigenin, metals (ruthenium), metal sols or other particulate sols (selenium, carbon, etc.), dansyl lysine, infra red dyes, coumarines (amino methyl coumarine), and antibodies, protein A, protein G, etc.

Figures 2A, 2B, 2C, 2D:
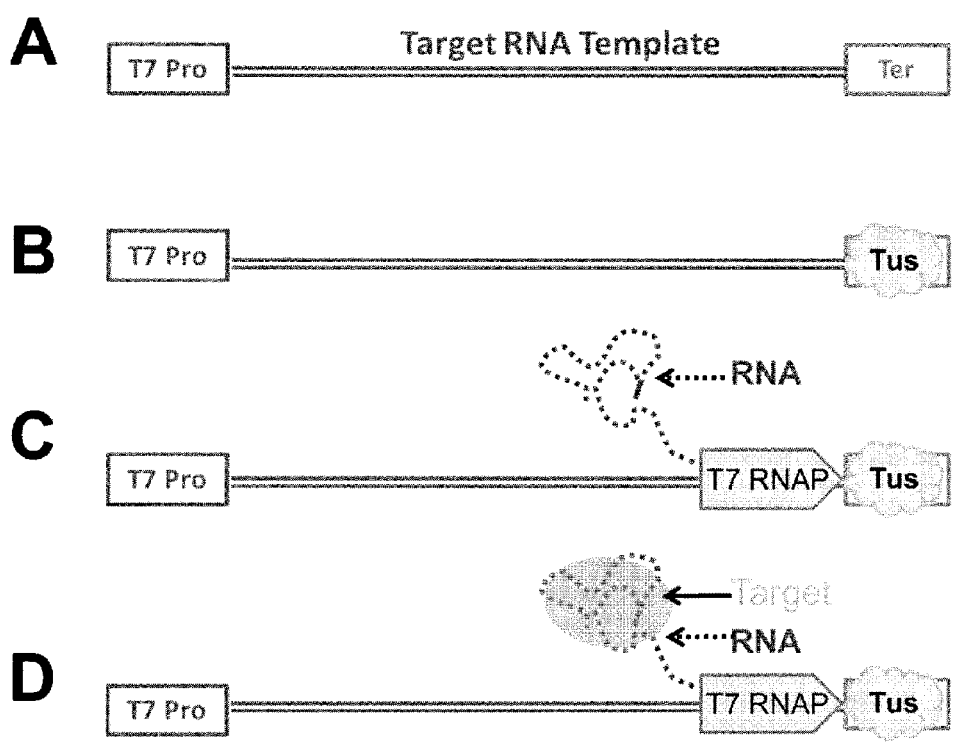
FIGS. 2A-2D show an example of the transcriptional halting process of the present invention using the bacterial replication terminator protein Tus as a T7 RNA polymerase blocking protein.

FIGS. 2A-2D show an exemplary nucleic acid construct and process of the present invention. FIG. 2A shows a map of a double stranded DNA template that contain a T7 promoter sequence ("T7 Pro") and a Ter-binding sequence that is specific for binding the bacterial replication terminator protein, Tus. To initiate the transcriptional halting process, Tus is provided and allowed to bind to its Ter binding site on the DNA template (FIG. 2B). T7 RNA polymerase is bound to the T7 promoter to initiate transcription (FIG. 2C). Transcription proceeds through the DNA template and is stably halted downstream of the Tus bound Ter site. Finally, a labeled second molecule, i.e., a target RNA interaction factor ("Target") is bound to the halted and tethered RNA transcript and the interaction is subsequently detected based on the detectable label of the second molecule.

The method of the present invention can be carried out in solution or coupled to a solid support, i.e., the DNA template or other component of the process is coupled to a suitable solid support. The substrate of the solid support may be biological, nonbiological, organic, inorganic, or a combination of any of these, with the solid support existing as particles, strands, precipitates, gels, sheets, tubing, beads, spheres, containers, capillaries, pads, slices, films, plates, slides, discs, membranes, etc. The solid support may have any convenient shape, such as a disc, square, circle, etc, and may contain raised or depressed regions suitable for immobilization of nucleic acid templates of the present invention.

Figures 3A, 3B, 3C, 3D, 3E, 3F:
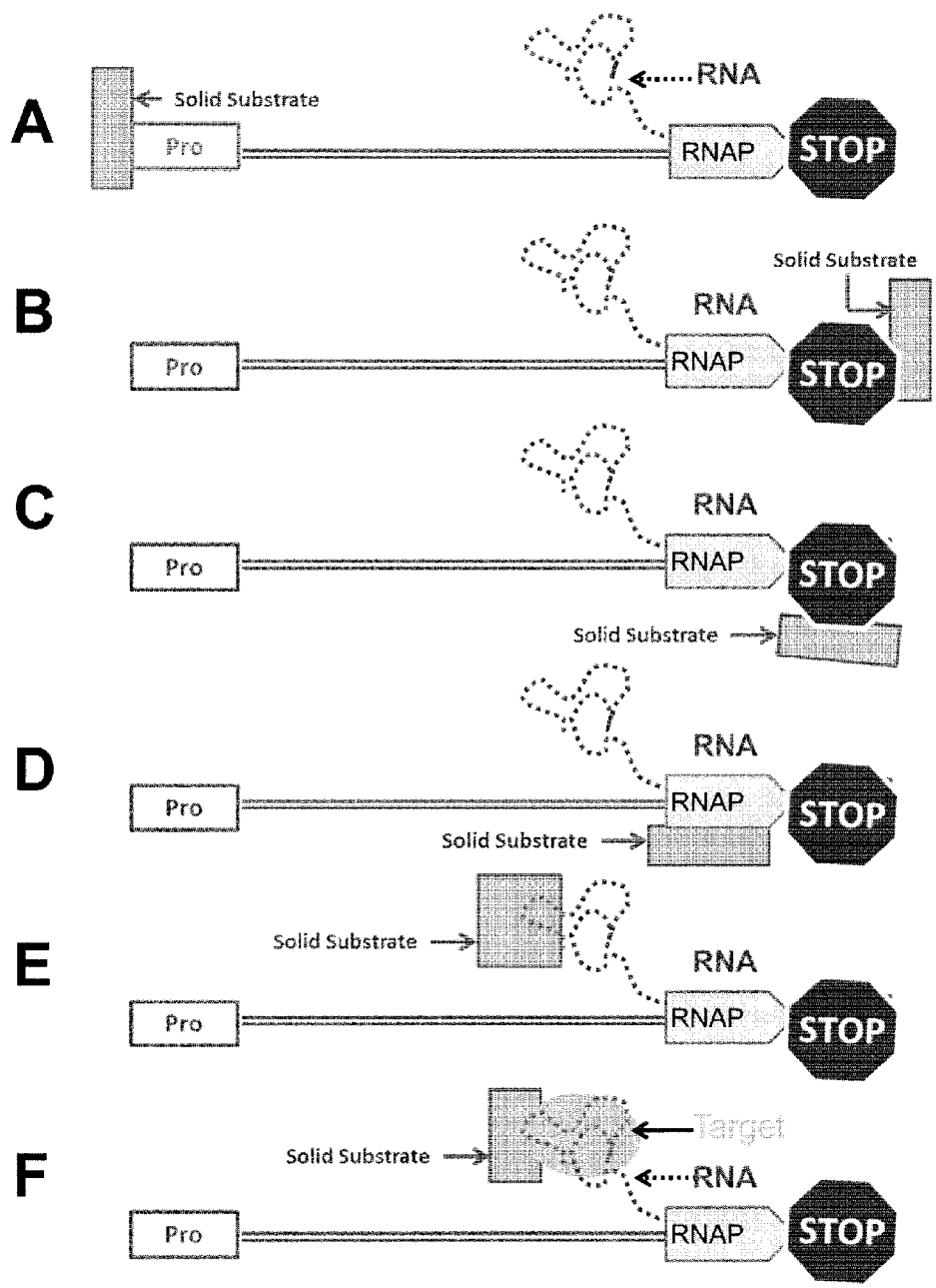
FIGS. 3A-3F show various scenarios for coupling the transcriptional halting process of the present invention to a solid substrate.

Coupling of the DNA template or other component of the process to a suitable solid support can be achieved by covalent linkage or by noncovalent interaction. FIGS. 3A-3F illustrate a number of alternative ways in which the process of the present invention can be coupled to the solid support. FIG. 3A shows an example of anchoring the nucleic acid construct to a solid substrate at the end of the template distal to the RNA polymerase blocking site (i.e., coupling via the 5' end of the DNA template). FIG. 3B depicts an example of anchoring the DNA template to a solid support at the template end proximal to the RNA polymerase blocking site (i.e., coupling via the 3' end of the DNA template). Immobilization of the DNA template to a solid support can be achieved using either a covalent linkage or noncovalent linkage (e.g., biotinylated DNA bound to avidin coated beads). Immobilization of the DNA template to a solid support can also be achieved indirectly, i.e., via the blocking group (e.g., the DNA binding protein) as shown in FIG. 3C, via the RNA transcript (FIG. 3E; e.g., bromo-UTP used during transcription to produce an RNA transcript that can be bound by an anti-BrUTP containing solid support), the RNA polymerase (FIG. 3D), or a factor bound to the RNA transcript (FIG. 3F). Again, such a linkage can be either covalent or noncovalent, with noncovalent linkages being inducible at any step in the transcription halting process. The use of affinity tagged proteins is especially convenient in this case as the proteins (e.g., DNA binding proteins) used in this process can readily be expressed as fusions with a suitable binding tag to facilitate immobilization to solid support containing the corresponding capture binding moiety. Suitable capture moieties and binding tag partners that can be used in accordance with this embodiment of the present invention include, without limitation, biotin and streptavidin, maltose and maltose binding protein, chitin and chitin binding protein, amylase and MBP, glutathione transferase and glutathione-S-transferase, histag and Ni-NTA matrix, and integrin and integrin binding peptides. Methods of covalently attaching oligonucleotides to a solid support are well known in the art, see e.g., Gosh and Musso, "Covalent Attachment of Oligonucleotides to Solid Supports," *Nucleic Acids Res.* 15(13): 5353-5372 (1987), Joos et al., "Covalent Attachment of Hybridizable Oligonucleotides to Glass Supports," *Anal. Biochem.* 247(1):96-101 (1997); Lund et al., "Assessment of Methods for Covalent Binding of Nucleic Acids to Magnetic Beads, Dynabeads, and the Characteristics of the Bound Nucleic Acids in Hybridization Reactions," *Nucleic Acids Res.* 16(22):10861-80 (1988), which are hereby incorporated by reference in their entirety.

Once transcription halting is achieved, the transcription reaction mix can be washed away from the solid support to give pure halted transcription complexes. In the case of DNA templates that are coupled to a solid support, this simply involves exchanging the solution in which the substrate is immersed.

When the transcriptional halting process is carried out with a halting template immobilized on a solid support such as beads, particles, cylinders, etc., the halted complexes with a tethered RNA transcript bound by a labeled second molecule can be readily sorted or separated based on the detectable label of the second molecule. For example and as demonstrated in the Examples herein, polystyrene beads containing PCR amplified clusters of DNA template were subject to the transcriptional halting process of the present invention to produce halted complexes containing tethered RNA molecules of interest. Following the addition of fluorescently labeled RNA interacting molecules, the beads were sorted by FACS. This method of sorting can be employed to readily purify or enrich for halted complexes bound by a second molecule to facilitate further analysis. Alternatively, sorting or selection can be based on other metrics as well, for example binding that enhances the fluorescence of a dye. By sorting based on intensity of that dye, one selects not only for binding but also for enhancement of the fluorescence of that dye resulting from the particular binding interaction (e.g., aptamer binding to target can restrict the dye to a conformation that is more competent for fluorescence).

The method of the present invention can further include sequencing of the RNA transcript of interest, either prior to transcriptional halting process, or subsequent to this step. In one embodiment of the present invention, sequencing of the DNA template encoding the RNA molecule of interest is achieved by coupling the process to a high-throughput sequencing method known in the art (see e.g., Metzker et al., "Sequencing Technologies—The Next Generation," *Nature Rev.* 11:31-46 (2010) and Voelkerding et al., "Next Generation Sequencing for Clinical Diagnostics-Principles and Application to Targeted Resequencing for Hypertrophic Cardiomyopathy," *J. Mol. Diagn.* 12: 539-551 (2010), which are hereby incorporated by reference in their entirety). For example, both the Illumina® Genome Analyzer and Roche® 454 sequencing platforms incorporate a modified PCR reaction (isothermal amplification with both DNA oligonucleotide primers coupled to a glass slide and emulsion PCR with one of the DNA oligonucleotide primers coupled to polystyrene beads, respectively) to generate entities, or clusters of thousands of identical DNA templates grouped together on a solid substrate that are subsequently imaged for sequencing purposes. This amplification of a single DNA molecule to give thousands of identical molecules facilitates measurements in which the behavior of that population is representative of that single sequence and helps the sensitivity of detection by boosting the signal. These population measurements are used to very accurately determine the sequence of the DNA from which the population was derived. These systems can also be used to measure other properties of the DNA sequences that make up these small populations. The Illumina® platform is particularly amenable to this task; it provides a versatile and programmable tool for automatically imaging and analyzing occupancy of any fluorescently labeled entity bound to the DNA clusters that are used in sequencing. Accordingly, this system has been utilized previously to determine the affinity of fluorescently labeled DNA binding proteins to cluster sequences (Nutiu et al., "Direct Measurement of DNA Affinity Landscapes on a High-Throughput Sequencing Instrument," *Nat. Biotechnol.* 29(7):659-664 (2011), which is hereby incorporated by reference in its entirety).

In accordance with this embodiment of the present invention, the DNA halting template is amplified and coupled to the Roche® 454 beads, Illumina® flowcell, or other similar sequencing platform using PCR. Following sequencing of the DNA halting template, the DNA strand generated during sequencing is stripped away and a new second strand is generated using Klenow enzyme. The polymerase blocking site is functionalized, and RNA transcription initiated upon introduction of an appropriate RNA polymerase. Transcription is halted once the RNA polymerase reaches the blocking site, and the tethered RNA transcript encoded by individual DNA templates of each cluster is stably linked to that cluster so that the binding of other factors to the RNAs can be observed by imaging or other means. Much like the way in which an ensemble measurement of the population of identical DNAs is used to derive the sequence, the behavior of this population of RNAs is representative of the single sequence at the cluster. Tens of millions of these binding events can be imaged automatically in the sequencer.

In another embodiment of the present invention, the RNA template is directly sequenced following the transcriptional halting process, either prior to or after the introduction of the second molecule. Methods of direct RNA sequencing are known in the art, see e.g., Ozsolak et al., "Transcriptome Profiling Using Single-Molecule Direct RNA Sequencing," *Methods Mol. Biol.* 733: 51-61 (2011); Ozsolak and Milos, "Single-Molecule Direct RNA Sequencing without cDNA Synthesis," *Wiley Interdiscip. Rev. RNA* 2(4):565-70 (2011); and Ozsolak et al., "Direct RNA Sequencing," *Nature* 461 (7265): 814-18 (2009), which are hereby incorporated by reference in their entirety.

In addition to identifying RNA binding factors, experiments can be tailored to measure several parameters of this binding. For example, the affinity of the RNA encoded by these clusters to a bound factor can also be readily determined. A flowcell or plurality of beads containing immobilized DNA clusters with halted RNA transcripts is washed and exposed to increasing concentrations of a labeled candidate RNA interacting molecule, e.g., a labeled protein, peptide, or other molecule of interest. The fluorescence intensity of each cluster at each concentration of labeled factor is measured and then fit to a Hill equation to calculate the binding affinity or equilibrium dissociation constant (Kd) between the RNA transcript and the labeled protein, peptide, or other molecule of interest. For example, sequential binding at increasing concentrations gives a binding curve which can be fit to a Hill equation and used to solve the equilibrium dissociation constant ($K_d$) of the interaction. While any number of Hill equations routinely used in biochemistry could be used to solve the dissociation constant, a suitable equation is the following:

$$\text{Intensitiy} = b + \frac{m-b}{1+\left(\frac{K_d}{C}\right)^n}$$

Where b is the background fluorescence intensity at the cluster, m is the maximum fluorescence intensity (when all RNAs are occupied), $K_d$ is the dissociation constant, n is the Hill coefficient, and C is the concentration of target protein. The intensities measured by imaging at several different concentrations are then used to solve m, b, $K_d$, and n in a non-linear least squares or other suitable fitting routine. To give a more accurate fit, intensities used can be corrected for loss of signal, due to photobleaching or dissociation of halted RNAs, for example.

After determining the equilibrium dissociation constant for each RNA, both on/off rate constants can be experimentally determined. To determine the on rate, $k_{on}$, the association of newly labeled RNA transcript is measured through time, and intensities (from fluorescence or any other measure of occupancy) fit to an appropriate equation. For $k_{off}$, one would start with halted RNAs that are fully occupied by the labeled factor of interest. The solution in the flowcell or surrounding the beads is then exchanged for one lacking the labeled RNA binding moiety and sequential intensity measurements of halted RNAs are then fit using an appropriate model function to determine the off rate.

Another aspect of the present invention is directed to a kit for detecting an interaction between a ribonucleic acid (RNA) molecule and a second molecule. The kit contains one or more isolated nucleic acid constructs, each nucleic acid construct comprising a promoter sequence recognized by an RNA polymerase, a nucleotide sequence encoding an RNA molecule, and an RNA polymerase blocking site located 3' of the nucleotide sequence encoding the RNA molecule.

Suitable nucleic acid constructs containing RNA polymerase promoter sequences, RNA molecules, and an RNA polymerase blocking sites are disclosed supra. A kit of the present invention may contain more than one or a plurality of different types of nucleic acid constructs, where each type of nucleic acid construct differs by the nucleotide sequence encoding the RNA molecule, i.e., each type of nucleic acid construct produces a different RNA transcript but may have the same promoter and polymerase blocking site. For example, the kit may contain a library of nucleic acid constructs encoding a plurality of different RNA molecules (e.g., aptamer molecules) to facilitate multiplexed screening of RNA molecule-target molecule interactions.

The kit of the present invention may further comprise a solid support. The solid support is suitable for immobilization of the nucleic acid constructs of the kit via either a covalent or non-covalent attachment as described supra. Suitable solid supports are described supra, and include, without limitation particles, strands, precipitates, gels, sheets, tubing, beads, spheres, containers, capillaries, pads, slices, films, plates, slides, discs, membranes. The kit may further include reagents suitable to immobilize the nucleic acid constructs on the solid support, e.g., binding tag and capture moiety partners as described above, oligonucleotide primers, or reagents suitable for functionalizing the solid support and/or the nucleic acid constructs to achieve covalent attachment of the constructs to the support.

The kit of the present invention may further include one or more second molecules, i.e., potential RNA interacting factors. Suitable second molecules include proteins, polypeptides, or peptides, lipids, DNA molecules, RNA molecules, small molecules, or macromolecules. Preferably the second molecule contains a detectable label. In some embodiments, kits of the present invention contain libraries of second molecules.

The kit of the present invention may further include an RNA polymerase, ribonucleotide triphosphates, and any other component required for carrying out in vitro transcription of the nucleic acid constructs of the kit. Similarly, the kit of the present invention may further include reagents suitable for sequencing the nucleic acid construct or any portion thereof, e.g., the DNA template, prior to or after transcription. Suitable reagents depend on the method of sequencing and are well known in the art.

Another aspect of the present invention is directed to a method for screening a library of candidate compounds to identify a compound that binds to a target RNA molecule. This method involves providing a library of candidate compounds, and providing an isolated RNA transcript of the target RNA molecule tethered to a nucleic acid construct. The library of candidate compounds is contacted with the isolated RNA transcript tethered to the nucleic acid construct under conditions effective for one or more candidate compounds to bind to the RNA transcript. The method further involves detecting a binding interaction between one or more of the candidate compounds and the isolated RNA transcript tethered to the nucleic acid construct, and identifying the one or more candidate compounds that bind to the target RNA molecule based on the detection.

In accordance with this aspect of the present invention, an isolated RNA transcript of the target RNA molecule tethered to a nucleic acid construct is produced as described supra, i.e., transcribing a nucleic acid construct comprising a promoter sequence, a nucleotide sequence encoding the RNA molecule, and an RNA polymerase blocking site that is 3' to the nucleotide sequence encoding the RNA molecule in vitro to produce an RNA transcript corresponding to the RNA molecule. RNA transcription is halted by the RNA polymerase blocking site of the nucleic acid construct thereby tethering the RNA transcript to the nucleic acid construct. The RNA transcript tethered to the nucleic acid construct can be purified prior to screening with the library of candidate compounds.

The library of candidate compounds may be a library of proteins, polypeptides, peptides, lipids, DNA or RNA molecules (e.g., random sequence libraries, aptamer libraries generated by SELEX, random genomic fragments, and targeted genomic libraries (such as mRNAs, ncRNA, enhancer regions, promoter proximally paused RNAs, or pre-mRNAs), small molecules, or macromolecules. Preferably, the candidate compounds of the library contain a detectable label or tag, e.g., a fluorescent, luminescent, or radioactive tag as described supra.

In accordance with this aspect of the present invention, compound library screening can be coupled with high-throughput sequencing to enable sequencing of the nucleic acid template molecule prior to detection of the RNA-candidate compound interaction. In addition, to detecting and identifying binding interactions, binding affinities (i.e., binding and disassociation rates) can also be readily determined as described above.

EXAMPLES

The following examples are provided to illustrate embodiments of the present invention but they are by no means intended to limit its scope.

Example 1—Reagents and Proteins

The following buffers were used for the experiments described herein: 1×T7 Transcription buffer is composed of 30 mM HEPES pH 7.8, 80 mM Potassium Glutamate, 15 mM MgAc, 0.25 mM EDTA, 5 mM DTT, 0.05% Tween-20, 2 mM Spermidine; Tus binding buffer is composed of 10×T7 transcription buffer, 32.4 µM GST-Tus, and DEPC water; multiple round transcription mix is composed of 10×T7 transcription buffer, 0.1 units/µL, YIPP, superase inhibitor, 2.5 mM rNTP mix, T7 RNAP (4 mg/mL) and DEPC water; the klenow enzyme mix is composed of 10×NEB buffer 2, mM dNTPs, Klenow exo-enzyme (NEB), 20% tween, and DEPC water; GFP aptamer binding buffer is composed of 10×PBS, 1M $MgCl_2$, 20% Tween-20, superase inhibitor and DEPC water; primer rehybridization buffer is composed of 100 µM IllumFORAdapt-DBS-IllumFORSeq and Illumina® Hyb 1 Buffer. The following proteins used in these experiments were overexpressed in *E. coli* and purified by standard molecular biology techniques: 6×His-EGFP-mOrange, 6×His-EGFP, GST-Tus, 6×-His T7 RNA Polymerase, Taq DNA Polymerase.

Example 2—Electrophoretic Mobility Shift Assay (EMSA)

EMSA was performed to resolve DNAs engaged in different complexes with Tus, T7 RNA polymerase, and RNA. A DNA template containing the GFP aptamer template flanked by a T7 RNA polymerase promoter at the 5' end and a Tus binding element (Ter1) at the 3' end was prepared. This template was end labeled with $^{32}P$ using polynucleotide kinase with ATP γ $^{32}P$ as its substrate. The resulting solution was mixed with either water or GST-Tus at 100 times the concentration of DNA in 1×T7 transcription buffer and incubated at 37° C. for thirty minutes. An equal volume of 1×T7 transcription buffer was added to the template without Tus protein, and an equal volume of 1×T7 transcription buffer, with or without the components of a transcription reaction, was added to the templates with Tus protein and incubated at 37° C. for thirty minutes. 80% glycerol was then added to the samples to a concentration of 10%, and equal volumes of the resulting reactions were run on a 4% native polyacrylamide gel. The gel was then dried and imaged by autoradiography.

Figures 5A, 5B, 5C:
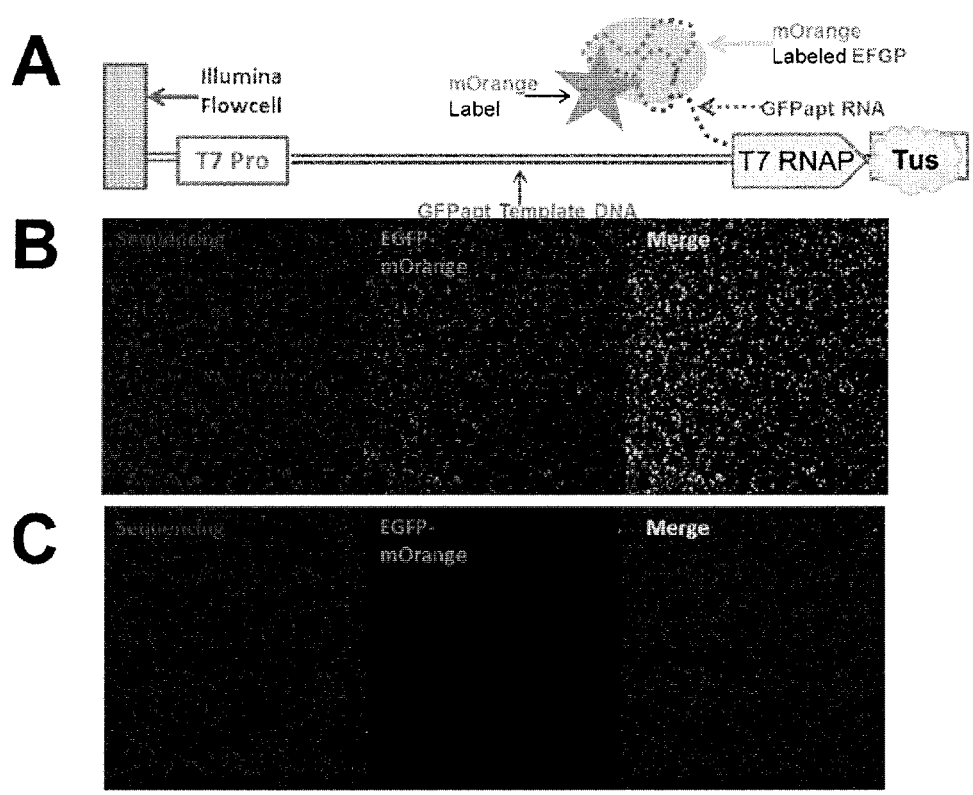
FIGS. 5A-5C show the detection of an RNA interaction in an Illumina®GAIIx sequencer using the method of the present invention.

Transcription halting and binding of RNA to protein on an Illumina® sequencer. Libraries for sequencing were prepared to contain an RNA template insert flanked by a 5' T7 promoter and 3' Ter binding site with the appropriate adaptors complimentary to the lawn of oligonucleotides on the Illumina® flowcell coupled to the extreme 5' and 3' ends. The Ter site was positioned 3' of the Illumina® sequencing primer site to ensure that the target RNA is fully emerged from the polymerase upon halting and so that sequencing begins with the target RNA. A standard sequencing run was performed with these libraries on an Illumina® GAIIx using an 82 cycle read on a paired end flowcell. The same XML program used for the sequencing included all subsequent steps to effect transcription halting and binding of EGFP-mOrange to the sequenced DNA clusters. First, the second strand generated during sequencing was stripped away with 0.1 N NaOH, leaving just single stranded DNA. The flowcell was then heated to 60° C., and primer annealing to the 3' end of the templates (covering the Ter site plus ~10 bp downstream) in Illumina® hybridization buffer (Hyb Buffer 1, Illumina® Inc.) was added. Excess primer was then washed away with 1×NEB buffer 4 with 0.01% Tween-20 (New England Biosciences). DNA was made completely double stranded by flowing in a Klenow exo-enzyme reaction mix (lx NEB Buffer 4, 0.01% Tween-20, 0.2 mM dNTPs, Klenow exo-) and incubating for 30 minutes at 37° C. The flowcell containing double stranded DNA clusters was equilibrated with 1×T7 transcription buffer. The flowcell was washed with 1 µM GST-Tus in 1×T7 transcription buffer. Tus was allowed to bind the DNA templates' Ter elements for 30 minutes at 37° C. The flowcell was then equilibrated with a transcription mix (1×T7 transcription buffer, 0.5 mM NTPs, T7 RNAP, YIPP, Superase Inhibitor, 0.5 µM GST-Tus). Transcription and halting was allowed to proceed for 30 minutes at 37° C. The flowcell was then equilibrated with GFP aptamer binding buffer at room temperature. It was promptly imaged, just as during sequencing. The flowcell was then equilibrated in successive, increasing concentrations of EGFP-mOrange in binding buffer and imaged at each concentration in equilibrium binding after 30 minutes equilibration at each concentration. Concentrations varied from 0.04 nM increasing up to 625 nM in fivefold increments. EGFP-mOrange is used because its interaction with the GFP aptamer is being measured; however, EGFP is not compatible with the optics of the sequencer, while mOrange is. FIGS. 5A-5B are images taken of DNA clusters labeled by Illumina® dyes during sequencing using the Illumina® SCS (left panel), images from EGFP-GFP aptamer binding after transcriptional halting at 625 nM EGFP-mOrange (middle panel), and finally a merge of the two images (right panel). Images are shown for two cases; in the first (FIG. 5B), all DNA clusters in the lane present had halted GFP aptamer RNA. In the second (FIG. 5C), all clusters present the SRB-2 aptamer RNA after transcription and halting.

Figure 6:
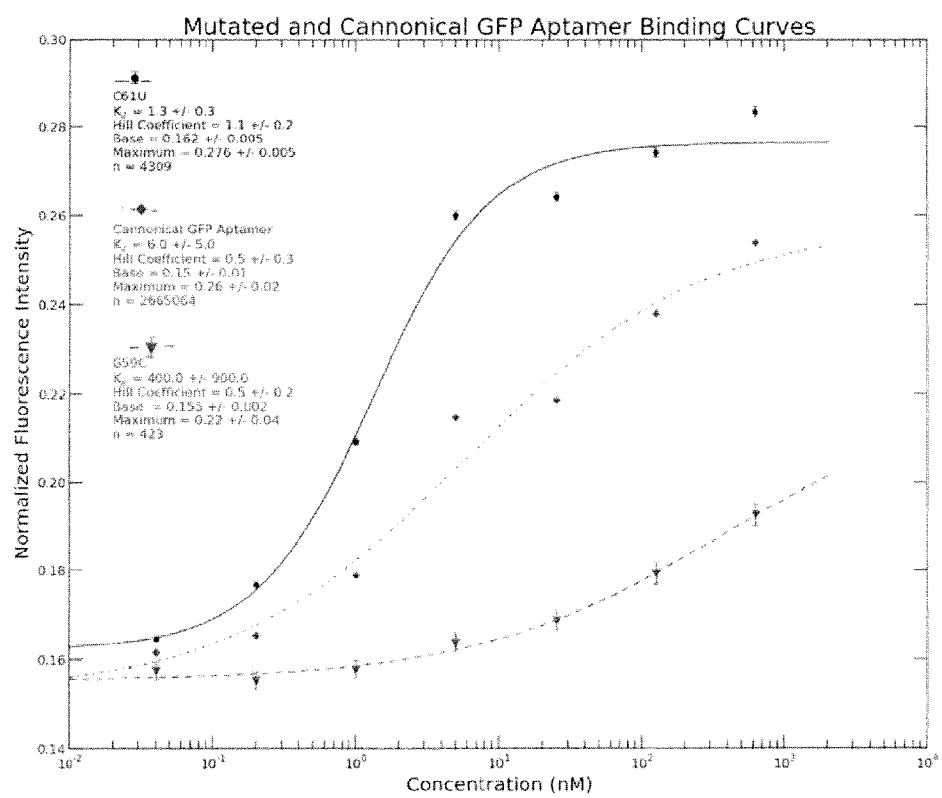
FIG. 6 is a graph showing sample binding curves of an RNA-protein interaction imaged in Illumina® GAIIx sequencer. This plot shows the measured fluorescence intensities for individual sequences in Illumina® GAIIx sequencer. Fluorescence intensities shown were normalized for cluster size and position by dividing protein binding intensity by the intensity from the sequencing run. Each curve represents the averaged intensities for multiple clusters with identical sequences (ranging from n=423 to n=2665064). The three sequences shown are: the canonical GFP aptamer (diamond, Kd=6.0+/−5.0 nM), a point mutant of the GFP aptamer with higher measured affinity (circle, Kd=1.3+/−0.3 nM), and a point mutant with low measured affinity (triangle, Kd=400.0+/−900.0 nM). The intensities of EGFP-mOrange were fit in a weighted least squares non-linear regression to the Hill equation described herein. The results of these fits are shown in the upper left corner of the plot. The measured affinity of the canonical GFP aptamer is consistent with published results (Kd=5.1 nM) (Shui B. et al., "RNA Aptamers that Functionally Interact with Green Fluorescent Protein and its Derivatives," *Nucleic Acids Res.* 40(5): e39 (2012), which is hereby incorporated by reference in its entirety).
Figure 7:
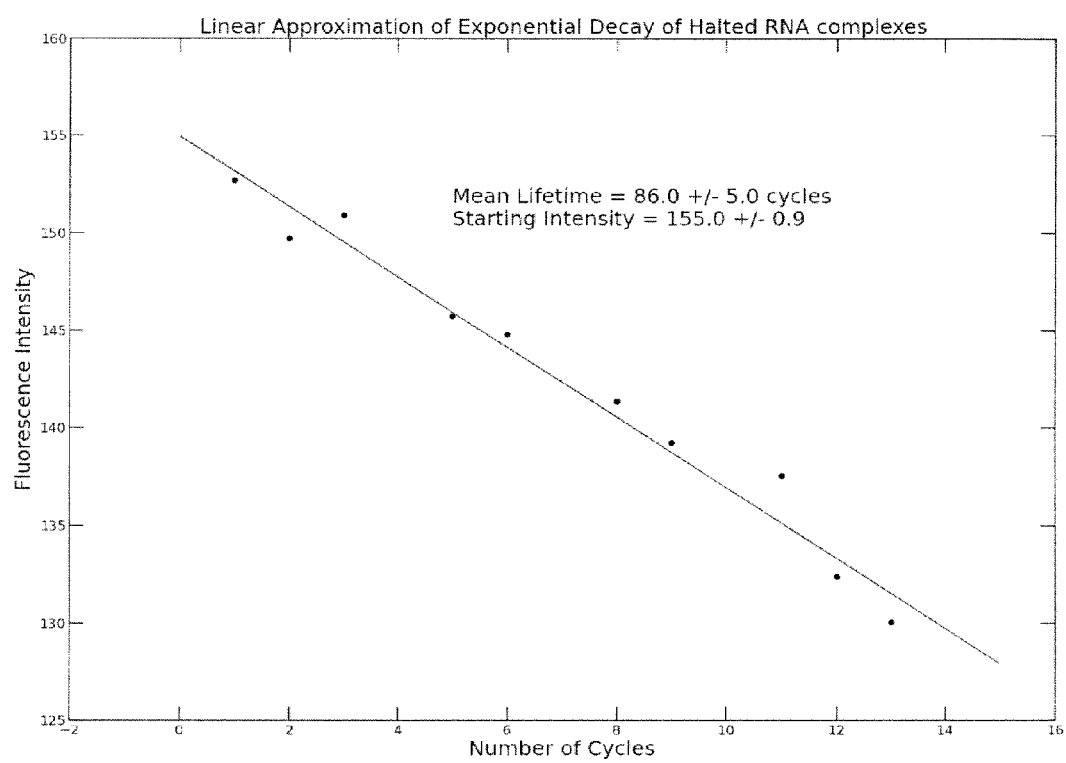
FIG. 7 shows the characteristic lifetime of halted RNA complexes. Experimental setup is the same as described in FIG. 5B. Here, clusters were imaged ten successive times after reequilibrating with fresh EGFP-mOrange. Loss of signal is due to dissociation of halted RNA complexes. The raw fluorescence intensity of the average of 2.6 million GFP aptamer clusters is plotted against the number of imaging cycles. Each imaging cycle took approximately 1.5 hours. A linear approximation of the exponential decay of halted RNAs that is occurring was fit to the data. The following equation was used.

The flowcell was imaged ten successive times at 625 nM EGFP-mOrange (the highest concentration). Each time, the flowcell was equilibrated in protein solution for one half hour before imaging, just as during the binding curve. After three of these cycles, imaging was not carried out, but rather the flowcell was allowed to sit in 625 nM EGFP-mOrange for the time that it would take for one equilibration and binding cycles. Thus, the ten imaging steps span the time that it would take for 13 equilibration and imaging steps. After the run, protein binding fluorescence intensities are extracted from the T channel of the .cif files generated by Illumina® SCS during sequencing. These are then matched by coordinates to the clusters' sequence in .cl files generated with the Illumina® offline basecaller for the same sequencing run. These intensities were then averaged across all clusters with each unique sequence, generating an average binding curve representative of each sequence. This was then fit to the Hill equation as described supra via a weighted least squares nonlinear regression in the Numpy module of Python. Three such binding curves are shown in FIG. 6, for the GFP aptamer, and two point mutants of the GFP aptamer. FIG. 7 shows the average protein binding intensities across the dissociation curve imaged as described above (the 10 imaging steps at the highest protein concentration).

Example 3—Transcription Halting on GST Beads

DNA templates were prepared with the GFP aptamer template flanked on the 5' end by a T7 promoter and 10 nt C-less cassette, and two Ter sites on its 3' end (FIG. 8A). First, these templates were bound to GST-Tus in 10× molar excess in 1×T7 transcription buffer for 30 minutes at 37° C. The resulting Tus-DNA complexes were incubated with glutathione coupled agarose beads in 1×T7 transcription buffer for 30 minutes at 37° C. (FIG. 8B) to achieve immobilization. An equal volume of 2× transcription solution lacking CTP was then added to the resulting bead slurry, and transcription was allowed to proceed for 30 minutes at 37° C. At this time, the chased beads were washed three times in 1×T7 transcription buffer. An equal volume of 2× transcription reaction mix lacking polymerase but containing CTP was added to the chased treatment but not the initiated control. Transcription was allowed to proceed for another 30 minutes at 37° C. The beads were washed three times with GFP aptamer binding buffer (1×PBS, 5 mM MgCl$_2$, 0.01% Tween-20). The washed beads were then incubated with 1 µM 6×His-EGFP for 30 minutes. Beads were then washed and imaged in a fluorescence microscope using a FITC filter. Both a DIC and fluorescence image of the two treatments are shown in FIG. 8C.

Example 4—Transcription and Halting on 454 Beads

Halting DNA templates compatible with the 454 sequence technology were made by incorporating the 454 adaptors on the templates used in the Illumina® experiments described in reference to FIGS. 5-7. These DNA halting templates were used to coat polystyrene beads in either all SRB-2 aptamer templates or GFP aptamer templates in a PCR reaction. A DNA oligonucleotide covalently linked to the bead was used as the forward primer and an oligonucleotide free in solution as the second primer. No emulsion was used, but rather the reaction was carried out in a single PCR reaction containing approximately 10$^6$ individual beads, as many beads coated in identical DNAs were wanted. These beads were washed with 1×T7 transcription buffer. Templates on the beads were then bound by 1 µM GST-Tus in 1×T7 transcription buffer. Templated beads were washed in transcription buffer and suspended in a transcription reaction (1×T7 transcription buffer, 0.5 mM NTPs, T7 RNAP, YIPP, Superase Inhibitor, 0.5 µM GST-Tus). After incubating 30 minutes at 37° C., the beads were washed with either GFP aptamer binding buffer or SRB-2 aptamer binding buffer (100 mM KCl, 5 mM MgCl$_2$, 10 mM HEPES pH 7.4, 0.01% Tween-20) and bound in either 1 µM 6×His-EGFP or 10 mM sulforhodamine B, respectively. After 20 minutes of binding at room temperature, beads were washed in the appropriate buffer. FIG. 9 shows micrographs of the SRB-2 and GFP halted RNA beads after this wash. Images were collected exactly as described for FIG. 8.

Example 5—Fluorescence-Activated Cell Sorting (FACS) of Halted Transcriptional Complexes The beads with halted GFP aptamer transcription complexes show in FIG. 9 were subjected to fluorescence activated cell sorting on a BD® FACS Aria cell sorting instrument. FIGS. 10A and 10B show traces in the FITC channel of the cell sorter (where GFP is visible). FIG. 10A shows negative control beads, which were not subjected to transcription as described for the beads in FIG. 9, but were bound to GFP and washed. FIG. 10B shows the traces for beads that were transcribed, halted, bound to GFP, and washed. The vertical bars labeled FITC only show the thresholds that were used in sorting beads that have halted GFP aptamer. GFP aptamer beads were then sorted into separate tubes on the instrument. In equal mixture sorting, GFP aptamer beads labeled by transcription halting and binding of EGFP to the GFP aptamer were sorted from a 1:1:1:1 mixture of GFP template beads:SRB-2 aptamer beads labeled by SRB:SRB-2 aptamer beads labeled by malachite green:random library beads. SRB-2 aptamer beads were labeled by nonspecific interaction of the dyes sulforhodamine and malachite green with the hydrophobic polystyrene beads. In rare GFP sorting, one drop of GFP aptamer beads was added to 500 µL of a mixture of equal amounts of sulforhodamine B or malachite green labeled SRB-2 aptamer beads. qPCR was used to quantify the level of enrichment of GFP aptamer beads from the others in the mixtures described supra. This was done by amplifying the DNA covalently linked to the beads, which served as the template for transcription. To quantify enrichment above specific templates, both the starting and sorted pools were subjected to qPCR using primers specific to either the GFP aptamer or the SRB-2 aptamer. This was compared to standard of both templates to determine the concentration of each species in the bead samples. Enrichments are calculated as [Concentration of GFPapt in sorted sample/concentration of GFPapt in the starting pool]/[Concentration of SRB-2 apt in sorted sample/concentration of SRB-2 apt in the starting pool]. Similarly, to calculate enrichment over nonspecific DNA, a primer that anneals outside of the RNA template region and will thus amplify all DNA linked to the polystyrene beads was used instead of the SRB-2 aptamer specific primers.

Discussion of Examples 1-5

Figure 4:
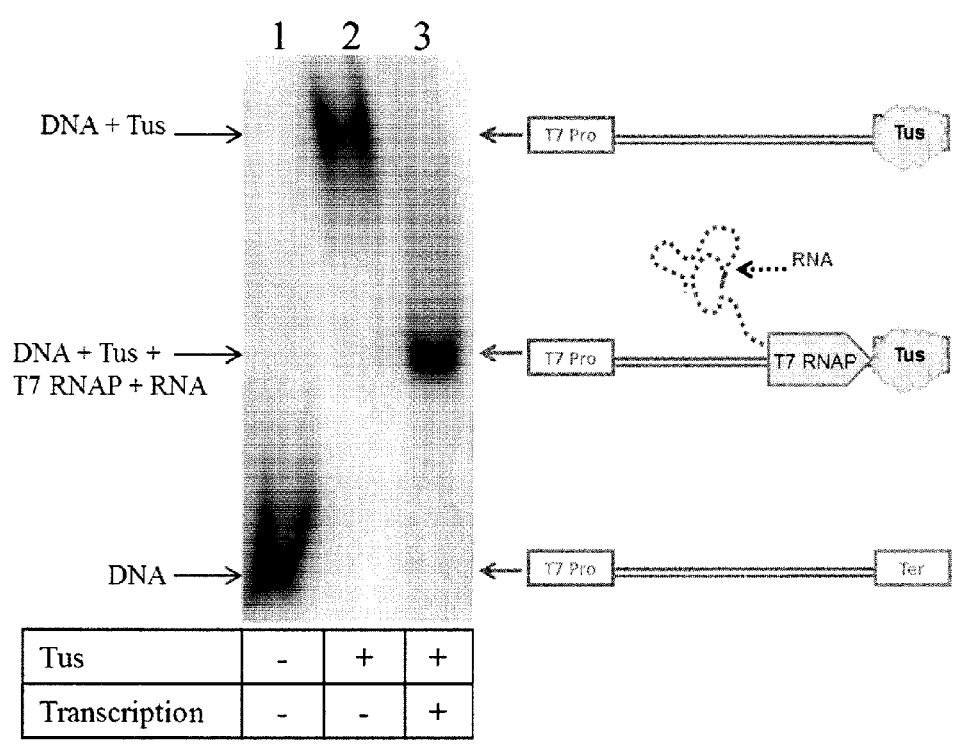
FIG. 4 demonstrates the efficiency of transcriptional halting by Tus bound Ter in an electrophoretic mobility shift assay. Equal amounts of radioactively labeled DNA template were added to each of the three lanes shown. Schematics from FIG. 2 are provided to show the composition of each detected complex. Lane 1 contains a DNA halting template having a T7 promoter sequence, DNA template encoding an RNA of interest, and Tus binding sequence (Ter). Lane 2 contains the same template as Lane 1 with one Tus molecule bound to the template's Ter sequence. The added mass of Tus retards the DNA's mobility through the gel causing it to shift. Lane 3 shows the complex after transcription. The addition of T7 RNA polymerase and RNA to the complex in lane 2 increases the mobility of the labeled DNA through the gel, due to the added charge of the RNA. The absence of a Tus+DNA band in lane 3 indicates that most DNA templates are in a stable complex with halted RNA.

To demonstrate the utility of the transcriptional halting method of the present invention, a nucleic acid construct comprising the T7 promoter sequences, a nucleotide sequence encoding a GFP aptamer ("GFPapt") and the *E. coli* DNA sequence element for Ter as the RNA polymerase roadblock was generated. The Ter-binding protein, Tus, can be purified by a number of molecular biology techniques for protein expression and purification. In this case, it was overexpressed in bacteria with a glutathione S-transferase (GST) tag and purified by affinity chromatography with glutathione coupled agarose resin. After the halting template was bound by Tus, transcription was carried out by adding T7 polymerase and all four NTPs to the solution. After multiple round transcription occurred, the different resulting DNA complexes were effectively separated from the rest of the transcription in the electro-mobility shift assay shown in FIG. 4. This electro-mobility shift assay shows that nearly one hundred percent of DNA templates are engaged in halted RNA complexes (FIG. 4). In each lane of FIG. 4, the only labeled component of the halted transcription complex is the DNA. In Lane 1, naked template, without Tus or transcription is run. In lane 2, GST-Tus protein has been added. Tus binds to the DNA's Ter sequence element, generating a bulkier complex and retarding its mobility through the gel matrix. After transcription, complexes containing DNA, Tus, T7 RNA polymerase, and RNA run at intermediate mobility. The fact that each lane contains a distinct single band shows that the processes of Tus binding to its DNA sequence element and of transcription halting of T7 RNA polymerase by Tus are extremely efficient. This invention is therefore capable of producing a halted transcription complex with an RNA molecule linked to its DNA template at the vast majority of DNAs in a solution. This means that it is robust enough for use in a myriad of applications. This process was tested for RNAs up to 1000 nt long, and the presence of RNA in the halted transcription complex was shown by collapse of the halted complex band upon digestion by RNase.

The competence of the resulting halted RNA for sequence specific interactions with other factors has been demonstrated by the ability of EGFP to be linked to solid substrate through a halted GFP aptamer complex in a variety of different circumstances as shown in FIGS. 5, 8, and 9. In FIG. 5, EGFP was bound to a glass flowcell in an Illumina® sequencing instrument via a halted GFP aptamer transcription complex covalently linked to the slide through the DNA template. The specificity of this interaction is shown by the inability of GFP to bind SRB-2 halted transcription complexes in the same flowcell (which also contain halted RNA). Thus, the interaction observed at GFP aptamer templates is due to the specific interaction of properly folded GFP aptamer with EGFP, rather than a nonspecific interaction with RNA or any other member of the complex. FIG. 9 is very similar, showing the same result, except that in this case, rather than being linked to an Illumina® flowcell, the DNA template of the halted GFP aptamer transcription complex is linked to a polystyrene bead, and EGFP is imaged directly (without the use of mOrange). FIG. 8 also shows the same result, though in a different way. In this case, the halted transcription complex is linked to agarose beads via a noncovalent interaction between the glutathione coupled to the beads with the GST domain of the Tus protein in the halted transcription complexes. This demonstrates that linkage to solid substrate can take place via any member of the halted transcription complex. Taken together, these results show that transcription halting produces RNAs that are competent for interactions with other factors, much as they would be in solution. Thus, the present invention provides a means for identifying and characterizing wide variety of RNA interactions.

The halted transcription complexes are long-lived. The characteristic lifetime of the stalled T7 polymerase complex is about 30 hours (FIG. 7). This shows that transcription halting produces RNAs that are stable enough for most any molecular biology technique to measure an interaction to be performed within the lifetime of the halted complex. Furthermore, the continuity of decay thorough the non-imaging cycles (at cycles 3, 5, and 10) shows that loss of signal is primarily due to dissociation of complexes and not photobleaching, likely because all bleached flours are exchanged for new in equilibrium. Thus, in assays with multiple measurements, it will likely only be necessary to include a single correction to the intensity observed for loss of signal.

The ability to measure the binding affinity between a halted RNA transcript (e.g., GFP aptamer) and a corresponding binding moiety (e.g., labeled EGFP) on an Illumina® GAIIx high throughput sequencing instrument was also demonstrated as shown in the binding curve of FIG. 6. The affinity of 6±5 nM determined in the sequencer agrees with the affinities of between 5 and 15 nM determined by isothermal calorimetry and electromobility shift assay, respectively. Furthermore, RNAs in a mutated GFP aptamer pool with poor measured affinity have significantly altered secondary structure predictions, demonstrating that this assay is sensitive to a range of different affinities.

FIG. 10 shows that an embodiment of this invention can be used to sort RNAs by affinity to a labeled protein. It is common in molecular biology to represent a single DNA sequence by many identical copies (in high throughput sequencing, for example). This strategy results in a phenomenon that is observable, whereas making the same measurement for a single molecule is nearly impossible. This is much harder to do for RNA. But by transcription halting, those techniques are bridged to apply to RNA as well. FIGS. 10A and 10B show that polystyrene beads can be resolved based on the association of fluorescently labeled protein to RNA engaged in halted transcription complexes linked to the beads. Furthermore, FIGS. 10C and 10D show that these beads are able to be sorted on this basis, resulting in high enrichment for beads whose halted RNA binds the protein, as evidenced by a high enrichment for GFP aptamer beads over SRB-2 aptamer beads based on GFP intensity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for detecting a binding interaction between a ribonucleic acid (RNA) molecule and a second molecule, said method comprising:
    forming a halted transcription complex in vitro, said complex comprising (i) a nucleic acid construct, said construct comprising a promoter sequence, a nucleotide sequence encoding the RNA molecule, and an RNA polymerase blocking site that is 3' to the nucleotide sequence encoding the RNA molecule, (ii) an RNA polymerase bound to the nucleic acid construct; (iii) an RNA transcript that is encoded by the nucleotide sequence of the nucleic acid construct and is tethered to the nucleic acid construct by the bound RNA polymerase, and (iv) an RNA polymerase blocking moiety bound to the RNA polymerase blocking site of the nucleic acid construct;
    providing the second molecule comprising a label, wherein said labeled second molecule or said halted transcription complex is coupled to a solid support;
    contacting, on the solid support, the halted transcription complex and the labeled second molecule under conditions effective for binding to occur between the tethered RNA transcript of said halted transcription complex and the labeled second molecule; and
    detecting, on the solid support, the labeled second molecule while bound to the tethered RNA transcript of the halted transcription complex.

2. The method of claim 1, wherein the second molecule is selected from the group consisting of a protein, a peptide, a lipid, a deoxyribonucleic acid (DNA) molecule, an RNA molecule, a small molecule, or a macromolecule.

3. The method of claim 1, wherein the promoter sequence comprises a nucleotide sequence suitable for RNA polymerase binding and initiation of transcription.

4. The method of claim 3, wherein the promoter sequence is selected from the group consisting of a T7 promoter sequence, T3 promoter sequence, SP6 promoter sequence, RNA Pol I promoter sequence, RNA Pol II promoter sequence, RNA Pol III promoter sequence, and E. coli RNA polymerase promoter sequence.

5. The method of claim 1, wherein said forming comprises:
    binding the nucleic acid construct to the RNA polymerase in the presence of ribonucleotide triphosphates (NTPs) under conditions effective for the bound RNA polymerase to transcribe the nucleotide sequence encoding the RNA molecule.

6. The method of claim 5, wherein said RNA polymerase is selected from the group consisting of T7 RNA polymerase, E. coli RNA polymerase, RNA Pol I, RNA Pol II, RNA Pol III, SP6, T3 RNA polymerase.

7. The method of claim 1, wherein the RNA polymerase blocking moiety is selected from the group consisting of a blocking group that is covalently bound to the RNA polymerase blocking site, a crosslinking molecule, and a DNA binding protein.

8. The method of claim 1, wherein the RNA polymerase blocking site is a DNA binding protein sequence and the RNA polymerase blocking moiety comprises one or more DNA binding proteins that specifically bind to said DNA binding protein sequence and block transcription by the RNA polymerase.

9. The method of claim 8, wherein the one or more DNA binding proteins is selected from the group consisting of LacI protein, EcoRI endonuclease non-cleaving mutant protein, polyoma virus T antigen, CCAAT box protein, TTFI, mycophage L5 repressor, and a bacterial replication terminator protein.

10. The method of claim 1 further comprising:
purifying the halted transcription complex having the RNA transcript tethered to the nucleic acid construct prior to said contacting.

11. The method of claim 1, wherein said second molecule comprises a label selected from the group consisting of a fluorescent label, a radiolabel, a chemiluminescent label, and a luminescent label.

12. The method of claim 1, wherein the nucleic acid construct or the tethered RNA transcript of the halted transcription complex is coupled to the solid support.

13. The method of claim 1, wherein the labeled second molecule is coupled to the solid support.

14. The method of claim 1, wherein the RNA polymerase of the halted transcription complex is coupled to the solid support.

15. The method of claim 1, wherein the RNA polymerase blocking moiety is coupled to the solid support.

16. The method of claim 1, wherein the RNA molecule is selected from the group consisting of a mRNA, ncRNA, pre-mRNA, microRNA, aptamer, an enhancer RNA, an RNA molecule having a random sequence, and a transcript of a genomic DNA fragment.

17. The method of claim 1 further comprising:
quantifying an association rate of the binding interaction between the tethered RNA transcript and the second molecule based on said contacting and detecting.

18. The method of claim 1 further comprising:
washing the tethered RNA transcript and the labeled second molecule after said detecting;
repeating said detecting after said washing; and
quantifying a disassociation rate of the binding interaction between the tethered RNA transcript and the labeled second molecule based on said repeating.

19. The method of claim 1, wherein a plurality of halted transcription complexes are formed and a plurality of labeled second molecules are provided allowing for the detection of a plurality of RNA transcript-second molecule binding interactions simultaneously.

20. The method of claim 1 further comprising:
sequencing the nucleic acid construct prior to or subsequent to said forming.

* * * * *

SEQUENCE LISTING

<160> NUMBER OF SEQ ID NOS: 7

<210> SEQ ID NO 1
<211> LENGTH: 19
<212> TYPE: DNA
<213> ORGANISM: Artificial
<220> FEATURE:
<223> OTHER INFORMATION: T7 promoter sequence

<400> SEQUENCE: 1
taatacgact cactatagg                                                19

<210> SEQ ID NO 2
<211> LENGTH: 19
<212> TYPE: DNA
<213> ORGANISM: Artificial
<220> FEATURE:
<223> OTHER INFORMATION: T3 promoter sequence

<400> SEQUENCE: 2
aattaaccct cactaaagg                                                19

<210> SEQ ID NO 3
<211> LENGTH: 19
<212> TYPE: DNA
<213> ORGANISM: Artificial
<220> FEATURE:
<223> OTHER INFORMATION: SP6 promoter sequence

<400> SEQUENCE: 3
atttaggtga cactataga                                                19

<210> SEQ ID NO 4
<211> LENGTH: 300
<212> TYPE: DNA
<213> ORGANISM: Artificial
<220> FEATURE:
<223> OTHER INFORMATION: RNA Pol I promoter sequence

<400> SEQUENCE: 4
acgggccggc ccctgcgtgt ggccagggcg gccgggaggg ctccccggcc cggcgctgtc      60
cccgcgtgtg tccttgggtt gaccagaggg ccccgggcgc tccgtgtgtg gctgcgatgg     120
tggcgttttt ggggacaggt gtccgtgtcg cgcgtcgcct gggccggcgg cgtggtcggt     180
gacgcgacct cccggccccg gggaggtata tctttcgctc cgagtcggca ttttgggccg     240
ccgggttatt gctgacacgc tgtcctctgg cgacctgtcg ctggagaggt tgggcctccg     300

<210> SEQ ID NO 5
<211> LENGTH: 155

```
<212> TYPE: DNA
<213> ORGANISM: Artificial
<220> FEATURE:
<223> OTHER INFORMATION: RNA Pol II promoter sequence

<400> SEQUENCE: 5
gctgcagaac ctctttccct atctggtgtc cgccgacggg accaccgtga cgtcgggcag      60
caccaaagac acgtcgttac aggctccgcc ttcctacgag gaaagtgttt ataattctgg     120
tggcaaagga ccgggaccac cgtcgtctga tgcat                                155

<210> SEQ ID NO 6
<211> LENGTH: 139
<212> TYPE: DNA
<213> ORGANISM: Artificial
<220> FEATURE:
<223> OTHER INFORMATION: RNA Pol III promoter sequence

<400> SEQUENCE: 6 acagggagt ggcgccctgc aatatttgca tgtcgctatg tgttctggga aatcaccata      60
aacgtgaaat gtctttggat ttgggaatct tataagttct tatgagacca ctctttccca    120
tagggcggag ggaagctca                                                 139

<210> SEQ ID NO 7
<211> LENGTH: 84
<212> TYPE: DNA
<213> ORGANISM: Artificial
<220> FEATURE:
<223> OTHER INFORMATION: E. coli RNA Pol promoter sequence

<400> SEQUENCE: 7
aattcatagt caacacgcac ggtgttagac atttatccct tgcggcgata gatttaacgt      60
atgagcacaa aaagaaacc attg                                             84
```